United States Patent
Yu et al.

(10) Patent No.: US 11,021,427 B2
(45) Date of Patent: Jun. 1, 2021

(54) PD(II)-CATALYZED ENANTIOSELECTIVE C—H ARYLATION OF FREE CARBOXYLIC ACIDS

(71) Applicant: The Scripps Research Institute, La Jolla, CA (US)

(72) Inventors: Jin-Quan Yu, San Diego, CA (US); Pengxiang Shen, San Diego, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 15/733,763

(22) PCT Filed: Apr. 17, 2019

(86) PCT No.: PCT/US2019/027914
§ 371 (c)(1),
(2) Date: Oct. 19, 2020

(87) PCT Pub. No.: WO2019/204477
PCT Pub. Date: Oct. 24, 2019

(65) Prior Publication Data
US 2021/0087131 A1    Mar. 25, 2021

Related U.S. Application Data

(60) Provisional application No. 62/659,866, filed on Apr. 19, 2018.

(51) Int. Cl.
| | |
|---|---|
| *C07C 51/353* | (2006.01) |
| *C07C 67/343* | (2006.01) |
| *C07C 201/12* | (2006.01) |
| *C07C 253/30* | (2006.01) |
| *C07F 9/40* | (2006.01) |
| *C07D 333/24* | (2006.01) |
| *C07D 209/49* | (2006.01) |
| *C07D 209/48* | (2006.01) |
| *B01J 31/22* | (2006.01) |
| *B01J 27/232* | (2006.01) |
| *C07D 307/54* | (2006.01) |

(52) U.S. Cl.
CPC .......... *C07C 51/353* (2013.01); *B01J 27/232* (2013.01); *B01J 31/2213* (2013.01); *C07C 67/343* (2013.01); *C07C 201/12* (2013.01); *C07C 253/30* (2013.01); *C07D 209/48* (2013.01); *C07D 209/49* (2013.01); *C07D 307/54* (2013.01); *C07D 333/24* (2013.01); *C07F 9/4071* (2013.01); *C07B 2200/07* (2013.01)

(58) Field of Classification Search
None
See application file for complete search history.

(56) References Cited

U.S. PATENT DOCUMENTS

| | | | |
|---|---|---|---|
| 6,057,456 A | 5/2000 | Hartwig et al. | |
| 2008/0255192 A1 | 10/2008 | Kaila et al. | |

FOREIGN PATENT DOCUMENTS

| | | |
|---|---|---|
| EP | 2119703 A1 | 11/2009 |
| WO | WO-2015131100 A1 | 9/2015 |
| WO | WO-2017165304 A2 | 9/2017 |
| WO | WO-2019204477 A1 | 10/2019 |

OTHER PUBLICATIONS

"International Application No. PCT/US2019/027914, International Search Report and Written Opinion dated Jul. 3, 2019", (dated Jul. 3, 2019), 6 pgs.

(Continued)

*Primary Examiner* — Joseph R Kosack
(74) *Attorney, Agent, or Firm* — Schwegman Lundberg & Woessner, P.A.

(57) ABSTRACT

The invention includes procedures for stereoselective β-acylation of carboxylic acids having a β-carbon atom. For example, stereoselective acylation procedures include the following reactions: (I)

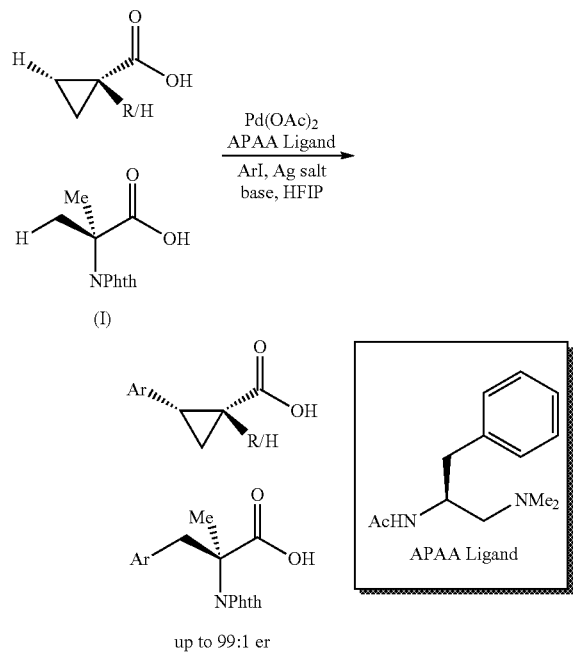

10 Claims, 1 Drawing Sheet

(56) References Cited

OTHER PUBLICATIONS

Chen, Kang, et al., "Development of Modifiable Bidentate Amino Oxazoline Directing Group for Pd-Catalyzed Arylation of Secondary C—H Bonds", Chemistry: A European Journal, vol. 21, Issue 20, 2015; pp. 7389-7393, (Mar. 24, 2015), 7389-7393.

Elling, Gary R., et al., "Cyclopropylarene chemistry. IV. Homoketenyl cations in a Friedel-Crafts acylation", J. Am. Chem. Soc. 1973, 95, 17, 5659-5662 [abstract only], (Aug. 1, 1973), 5659-5662.

Giri, Ramesh, et al., "Converting gem-Dimethyl Groups into Cyclopropanes via Pd-Catalyzed Sequential C—H Activation and Radical Cyclization", Org. Lett. 2006, 8, 25, 5685-5688 [abstract only], (Nov. 9, 2006), 5685-5688.

Giri, Ramesh, et al., "Palladium-Catalyzed Methylation and Arylation of sp2 and sp3 C—H Bonds in Simple Carboxylic Acids", J. Am Chem. Soc. 2007, 129 12, 3510-3511, (Mar. 3, 2007), 3510-3511.

Ishihara, Kazuaki, et al., "Design of an Organocatalyst for the Enantioselective Diels-Alder Reaction with a-Acyloxyacroleins", J. Am. Chem. Soc.2005, 127, 10504-10505 [abstract only], (Aug. 24, 2005), 10504-10505.

Jahngen, Edwin G.E., et al., "Dimerization of cyclopropanecarboxylic acid dianion and thermal decarboxylative rearrangement of the dimer to 2-cyclopropyl-4,5-dihydrofuran", J. Org. Chem. 1983, 48, 15, 2472-2476 [abstract only], (Jul. 1, 1983), 2472-2476.

Li, Jiuyuan, et al., "Chiral Primary-Tertiary Diamine Catalysts Derived From Natural Amino Acids for syn-Aldol Reactions of Hydroxy Ketones", J. Org. Chem. 2009, 74, 4, 1747-1750 [abstract only], (Jan. 16, 2009), 1747-1750.

Nagamine, Takashi, et al., "A new chiral synthesis of a bicyclic enedione containing a seven-membered ring mediated by a combination of chiral amine and bronsted acid", Heterocycles 76(2), 1191-1204 [abstract only], (Jun. 2, 2008), 1191-1204.

Schiefer, Isaac T., et al., "Inhibition of amyloidogenesis by non-steroidal anti-inflammatory drugs and their hybrid nitrates", J Med Chem. Apr. 14, 2011; 54(7): 2293-2306. doi:10.1021/jm101450p, (Apr. 14, 2011), 2293-2306.

Wasa, Masayuki, et al., "Pd(0)/PR3-Catalyzed Intermolecular Arylation of sp3 C—H Bonds", J am Chem Soc. Jul. 29, 2009; 131(29):9886-9887, (Jul. 29, 2009), 9886-9887.

Wasa, Masayuki, et al., "Pd(II)-Catalyzed Enantioselective C—H Activation of Cyclopropanes", J. Am. Chem. Soc. 2011, 133, 49, 19598-19601 [abstract only], (Nov. 7, 2011), 34 pgs.

Xiao, Kai-Jiong, et al., "Palladium(II)-Catalyzed Enantioselective C(sp3)-H Activation Using a Chiral Hydroxamic Acid Ligand", J. Am. Chem. Soc. 2014, 136, 8138-8142, (May 9, 2014), 8138-8142.

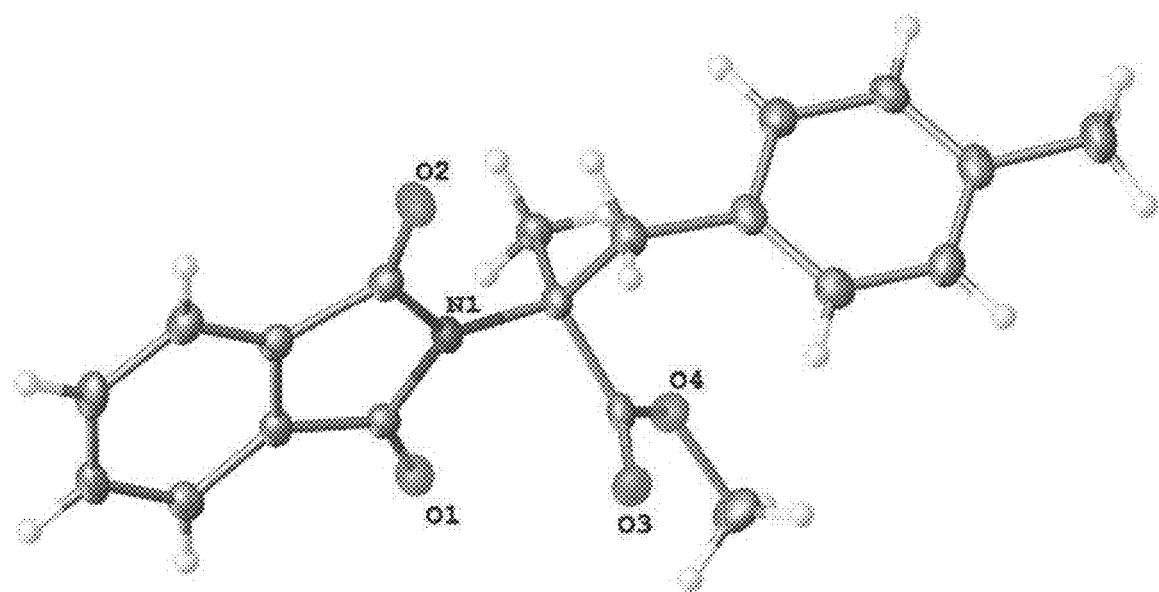

PD(II)-CATALYZED ENANTIOSELECTIVE C—H ARYLATION OF FREE CARBOXYLIC ACIDS

PRIORITY CLAIM TO RELATED APPLICATIONS

This application is a U.S. national stage filing under 35 U.S.C. § 371 from International Application No. PCT/US2019/027914, filed on 17 Apr. 2019, and published as WO2019/204477 on 24 Oct. 2019, which claims the benefit under 35 U.S.C. 119(e) to U.S. provisional application Ser. No. 62/659,866, filed on 19 Apr. 2018, the benefit of priority of each of which is claimed herein, and which applications and publication are hereby incorporated herein by reference in their entirety.

STATEMENT OF GOVERNMENT SUPPORT

This invention was made with government support under grant number GM084019 awarded by the National Institutes of Health. The government has certain rights in the invention.

BACKGROUND

Desymmetrization through C—H activation holds the potential to become a broadly useful chiral technology due to the widespread presence of symmetric prochiral $C(sp^3)$—H bonds in the majority of organic molecules.[1] Pd(II)-catalyzed enantioselective intermolecular $C(sp^3)$—H activation was recently made possible by a combination of weakly coordinating directing group and chiral bidentate ligand.[2,3,4,5] This strategy was firstly demonstrated by the development of N-perfluoroaryl amide-directed enantioselective C—H cross-coupling of α-quaternary cyclopropanecarboxamides using mono-N-protected amino acids (MPAA) as the chiral ligands.[2a] Recently, chiral bidentate quinoline ligands were developed to realize enantioselective functionalization of methylene $C(sp^3)$—H bond of acyclic N-perfluoroaryl carboxamides to construct β-chiral centers,[2c] while bidentate oxazoline ligands enabled enantioselective $C(sp^3)$-H functionalization of gem-dimethyl of N-perfluoroaryl or methoxy carboxamides for the construction of α-chiral centers.[2d] However, substrates in these reactions require ore-installed directing groups which need to be removed after C—H functionalization. Following the same notion of achieving protecting group free synthesis,[8] we embarked on the development of enantioselective C—H activation of carboxylic acids without using exogenous directing group.

SUMMARY

The invention is directed, in various embodiments, to procedures for stereoselective β-arylation of carboxylic acids having a β-hydrogen atom. For example, the invention can provide a method of stereoselective arylation of a β-carbon atom of a cyclopropane carboxylic acid having a δ-hydrogen atom, the cyclopropanecarboxylic acid having either an o-substituent or having an α-substituent, comprising contacting the cyclopropanecarboxylic acid and an aryl iodide in the presence of a catalytic quantity of a Pd(II) salt, a molar equivalent or more on an Ag(I) basis of an Ag(I) salt, and a molar equivalent or more of a base, in 1,1,1,3,3,3-hexafluoroisopropanol solvent, in the presence of an single enantiomer, either (R) or (S), of an acetyl-protected aminoethyl amine (APAA) ligand of formula

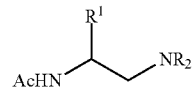

wherein Ac is acetyl, each R is independently selected methyl or ethyl, or the two R groups together with the nitrogen atom to which they are bonded form a 4- to 6-membered heterocyclyl ring; and wherein $R^1$ is an unsubstituted or substituted benzyl group, or wherein $R^1$ is a $(C_2-C_4)$-alkyl group;

to stereoselectively provide a β-aryl-cyclopropanecarboxylic acid, wherein the arylated β-carbon atom of the β-aryl-cyclopropanecarboxylic acid product, when no α-substituent is present is of an (R) or (S) single enantiomeric configuration, respectively, and When an α-substituent is present is of an (S) or (R) single enantiomeric configuration, respectively; an aryl group introduced being disposed cis to the carboxylic acid group of the cyclopropanecarboxylic acid.

A substrate cyclopropanecarboxylic acid can be of formula

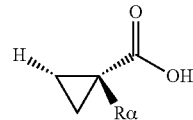

wherein Ra can be hydrogen (i.e., termed an α-unsubstituted cyclopropanecarboxylic acid herein), or can be a substituent, e.g., an alkyl, aryl, alkaryl, or heteroaryl group and the like, any of which can be further substituted with organic functional groups other than a carboxylic acid group (i.e., termed an α-substituted cyclopropanecarboxylic acid herein). If no other substituents are present, this precursor is achiral. When the stereoselective arylation reaction of the invention is carried out, a product of formula

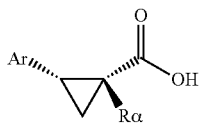

is obtained, the introduced aryl group being inserted cis to the carboxylic acid group, and stereoselectively such that when the ligand used is of the (S) absolute configuration, the β-carbon atom of the product from the unsubstituted cyclopropanecarboxylic acid precursor bearing an aryl group is of the (S) absolute configuration at that chiral center; and the β-carbon atom of the product from the substituted cyclopropanecarboxylic acid precursor bearing an aryl group is of the (R) absolute configuration at that chiral center.

The designation of the absolute configuration of the product β-arylcyclopropanecarboxylic acid as (S) or (R) in the product varies from the unsubstituted to the substituted case due to the change in the priority of groups bonded to the β-carbon atom under the Cahn-Ingold-Prelog group priority rules for assigning absolute configuration of (R) or (S) to a chiral center. The aryl group is introduced to the β-carbon atom via a Pd-ligand-substrate complex that is analogous between α-unsubstituted and α-substituted precursor cyclopropanecarboyxlic acids, but the presence of the o-substituent alters the naming protocol to provide the opposite (R) or (S) configuration assignment to that of the α-unsubstituted reaction product.

In other embodiments, the invention can provide a method of stereoselective arylation of a β-carbon atom of 2-phthalimidoisobutryic acid, comprising contacting the 2-phthalimidoisobutryic acid and an aryl iodide in the presence of a catalytic quantity of a Pd(II) salt, a molar equivalent or more on an Ag(I) basis of an Ag(I) salt, and a molar equivalent or more of a base, in 1,1,1,3.3,3-hexafluoroisopropanol (HFIP) solvent, in the presence of an single enantiomer, either (R) or (S), of an acetyl-protected aminoethyl amine (APAA) ligand of formula

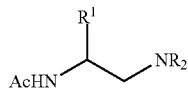

wherein Ac is acetyl, each R is independently selected methyl or ethyl, or the two R groups together with the nitrogen atom to which they are bonded form a 4- to 6-membered heterocyclyl ring; and wherein $R^1$ is an unsubstituted or substituted benzyl group, or wherein $R^1$ is a $(C_3$-$C_4)$-alkyl group, to stereoselectively provide a β-aryl-2-phthalimidoisobutryic acid, wherein the β-aryl-2-phthalimidoisobutryic acid product is of an (R) or (S) single enantiomeric configuration, respectively.

In carrying out a method of the invention, the APAA ligand can be of formula

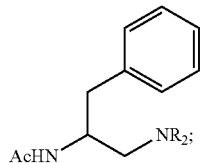

the Pd(II) salt can be Pd(OAc)$_2$; the carbonate base can be Na$_2$CO$_3$, or the Ag(I) salt can be Ag$_2$CO$_3$, or both.

For instance, the Pd(II) salt can be present at about 10 mole %, the ligand can be present at about 20 mole %, or both. The reaction can be carried out in HFIP, for example at about 80° C.,

BRIEF DESCRIPTION OF THE DRAWINGS

FIG. 1: X-ray structure of 7f.

DETAILED DESCRIPTION

Directed functionalization of C(sp$^3$)—H bonds of carboxylic acids without installing external directing group remains a significant challenge despite recent advances using pyridine/quinoline and MPAA ligands[7] These difficulties escalate in the development of enantioselective C—H activation reactions. First, C(sp$^3$)—H activation reactions of free carboxylic acids suffer from low reactivity due to the weak directing ability of the carboxyl groups. Second, the conformation of the metal-carboxylate complex is more flexible than that of the metal-amide directing group complex, which could cause problems for stereocontrol. Indeed, our previously developed bidentate acetyl-protected aminoethyl quinoline ligand only had limited success with a single special substrate, phthalyl-protected 1-aminocyclopropanecarboxylic acid.[2c] Therefore, we set out to develop a new type of ligands that could achieve more effective enantioselective control with free carboxylic acids. Herein we report the development of ethylenediamine derived chiral ligand that enables enantioselective C—H arylation of a broad range of cyclopropanecarboxylic acid, as well as the 2-aminoisobutyric acid.

Development of asymmetric syntheses of chiral cyclopropane[8] continues to attract attention because of their prevalence in biologically active natural products and pharmaceuticals.[9] We, therefore, selected cyclopropanecarboxylic acid as a model substrate for our ligand development. Notably, our previous enantioselective C—H coupling of cyclopropanecarboxamides with Ar-Bpin requires the presence of α-quaternary carbon centers.[2a, 10]

Based on our previous chiral bidentate MPAA quinoline, and oxazoline ligands, acetyl-protected amino group (NHAc) is a privileged moiety of chiral ligands for promoting C—H cleavage. We, therefore, decided to keep this motif intact while replacing the carboxyl, quinoline, and oxazoline with other σ-donor for chelation. Specifically, we synthesized a series of acetyl-protected aminoethyl amine (APAA) ligands to achieve enantioselective C(sp$^3$)—H functionalization of free carboxylic acids (Scheme 1, Table 1). First, various N-alkyl tertiary amine ligands were tested. Despite moderate background reaction in the absence of ligands (Table 1), effective binding of the ligands and possible ligand acceleration afforded significant enantioselectivity. Comparison of the results from L1 to L4 indicates that steric hindrance on the tertiary amine reduces the reactivity. For example, dilsopropylamine ligand only provided 8% yield of the product with almost no enantioselectivity, Cyclic amine ligand L5 and L6 are inferior in both reactivity and enantioselectivity. Notably, replacing acetyl with other protecting groups led to a complete loss of reactivity (L7-L10). Ligands with different side chains were also examined. Among different substituents, benzyl group (L1) gave the best yield of 82% and highest er of 97:3, while, isopropyl (L11), sec-butyl (L12) tert-butyl group (L13) and isobutyl (L14) gave slightly lower yield and enantioselectivity. Surprisingly, the ligand with phenyl group (LIS) provided only 20% yield and low enantioselectivity. Less hindered homobenzyl group (L16) also reduced the reactivity. and selectivity. Hence, we focused on the modification of the benzyl group.. Introducing substituent to the pare and ortho position on the phenyl group, as well as replacing phenyl with the naphthalenyl group lowered the yield (L17-L21). Finally, our previous three classes of chiral ligands all gave poor yields or enantioselectivity (L22-L23).

With the high-yielding and highly selective conditions in hand, we examined the scope of aryl iodides (Table 2). Majority of the aryl iodides containing electron-withdrawing and electron-donating group afforded desired products in good yields and high enantioselectivities (up to 98:2 er). Aryl iodides bearing electron-withdrawing groups such as para-methoxycarbonyl (3a), para-acetyl (3b), pare-trifluoromethyl (3d), meta-trifluoromethyl (3k) and ortho-methoxycarbonyl (3t) gave slightly higher yields than other aryl iodides. However, aryl iodide with a nitro group (3c) gave 53% yield of the product with 90:10 er. Iodobenzonitrile (3e) also afforded a lower yield but with high enantioselectivity. Notably, aryl iodides containing bromo (3h), phosphonate (3j), and aldehyde (3m) afforded the desired products in high yields and good enantioselectivity. Besides substituted phenyl iodides, heteroaryl iodides such as 2-acetyl-5-iodathiophene (3u) and 5-lodo-2-furaldehyde (3v) could also be tolerated in this reaction providing moderate yields and high er. The reaction using methyl iodobenzoate as the limiting reagent and a lower loading of silver salt also afforded a higher yield and enantioselectivity (3a).

Scheme 1: Bidentate Ligands Developed for Enantioselective C(sp³)—H Functionalization of Carboxylic Acids (present invention)

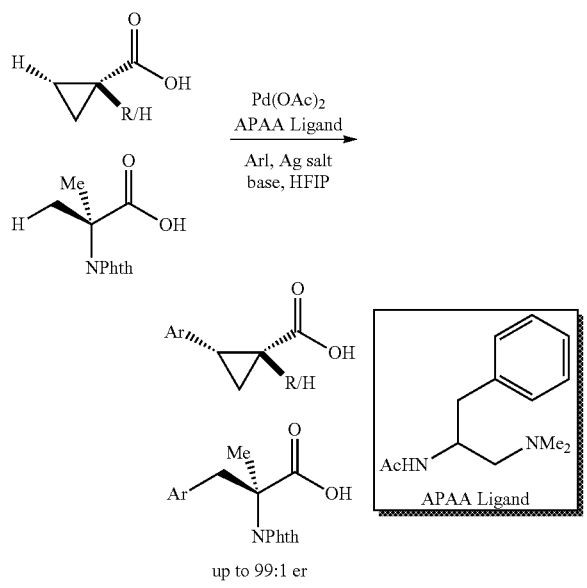

up to 99:1 er

The APAA ligand shown, of the (S) absolute configuration, yielded the cyclopropane-carboxylic acid of the (S) configuration at the arylated carbon atom, and yielded the (S)-enantiomer of the arylated phthalimidylisobutyric acid. The opposite enantiomer of the chiral ligand shown in Scheme 1 was also prepared and shown to be compatible with these substrates, albeit giving the corresponding products with the opposite enantiomer (the mirror image).

A wide range of α-substituted cyclopropanecarboxylic acids are also tested using methyl iodobenzoate the coupling partner (Table 3). 1-Aryl-1-cyclopropanecarboxylic acids (5a-d), which are an important motif in pharmaceutical chemistry,[11] were arylated to give the desired products in excellent yield and enantioselectivity. Interestingly, C(sp²)—H arylation of the α-phenyl groups did not occur. Chloro (5b), bromo (5c) and trifluoromethyl (5d) substituents on the phenyl group of substrates were all well tolerated in this reaction. α-Alkyl cyclepropanecarboxyiic acids are also suitable substrates for this reaction. Arylation of α-ethyl (5e), butyl (5f), and chioropentyl (5h) cyclopropanecarboxylic acids under 60°C. afforded the mono-arylated products in good yields and er. Surprisingly, α-phenylpropyl substitution reduced the yield to 58% (5g). Although α-Benzyl containing substrates (5i and 5j) decomposed under these conditions, replacement of $Ag_2CO_3$ with AgOAc provided desired products in moderate yield and high enantioselectivity. Benzyl-protected 1-hydroxymethyl (5k) and phthalyl-protected 1-aminomethyl cyclopropanecarboxylic acids (5i) provided good yield and excellent enantioselectivity. These ⊖-hydroxyl and β-amino-cyclopropanecarboxylic acid motifs are recurrent structures in bioactive molecules.[12]

TABLE 1

Ligand Screening for Enantioselective Arylation of Cyclopropanecarboxylic Acid[a,b]

| L1 | L2 | L3 | L4 |
|---|---|---|---|
| 82% yield, 97:3 er | 77% yield, 95:5 er | 40% yield, 87:13 er | 8% yield, 56:44 er |
| L5 | L6 | L7 | L8 |
| 55% yield, 83:17 er | 15% yield, 88:12 er | N.R. | N.R. |

TABLE 1-continued

Ligand Screening for Enantioselective Arylation of Cyclopropanecarboxylic Acid[a,b]

| Ligand | Result |
|---|---|
| L9 (BocHN, NMe2, benzyl) | N.R. |
| L10 (CbzHN, NMe2, benzyl) | N.R. |
| L11 (AcHN, NMe2, iPr) | 71% yield, 96:4 er |
| L12 (AcHN, NMe2, sec-Bu) | 76% yield, 96:4 er |
| L13 (AcHN, NMe2, tBu) | 64% yield, 94:6 er |
| L14 (AcHN, NMe2, iBu) | 62% yield, 96:4 er |
| L15 (AcHN, NMe2, Ph) | 20% yield, 78:22 er |
| L16 (AcHN, NMe2, CH2CH2Ph) | 49% yield, 91:9 er |
| L17 (4-OMe-benzyl) | 32% yield, 93:7 er |
| L18 (2,6-F2-benzyl) | 56% yield, 96:4 er |
| L19 (2,6-Ph2-benzyl) | 67% yield, 95:5 er |
| L20 (2-naphthylmethyl) | 52% yield, 91:9 er |
| L21 (1-naphthylmethyl) | 51% yield, 95:5 er |
| L22 (AcHN-Phe-OH) | 45% yield, 84:16 er |
| L23 (oxazoline) | 44% yield, 89:11 er |
| L24 (quinoline, 3,5-tBu2-phenyl) | 61% yield, 52:48 er |

No Ligand
30% yield

[a]Conditions: 1 (0.2 mmol), 2a (2.0 equiv), Pd(OAc)2 (10 mol %), ligand (20 mol %), Ag2CO3 (1.5 equiv), Na2CO3 (1.5 equiv), HFIP (0.25 mL), 80° C., air, 16 h.
[b]1H NMR yields, using CH2Br2 as an internal standard.

TABLE 2
The Scope of Aryl Iodides for Enantioselective Arylation of Cyclopropanocarboxylic Acid[a,b]
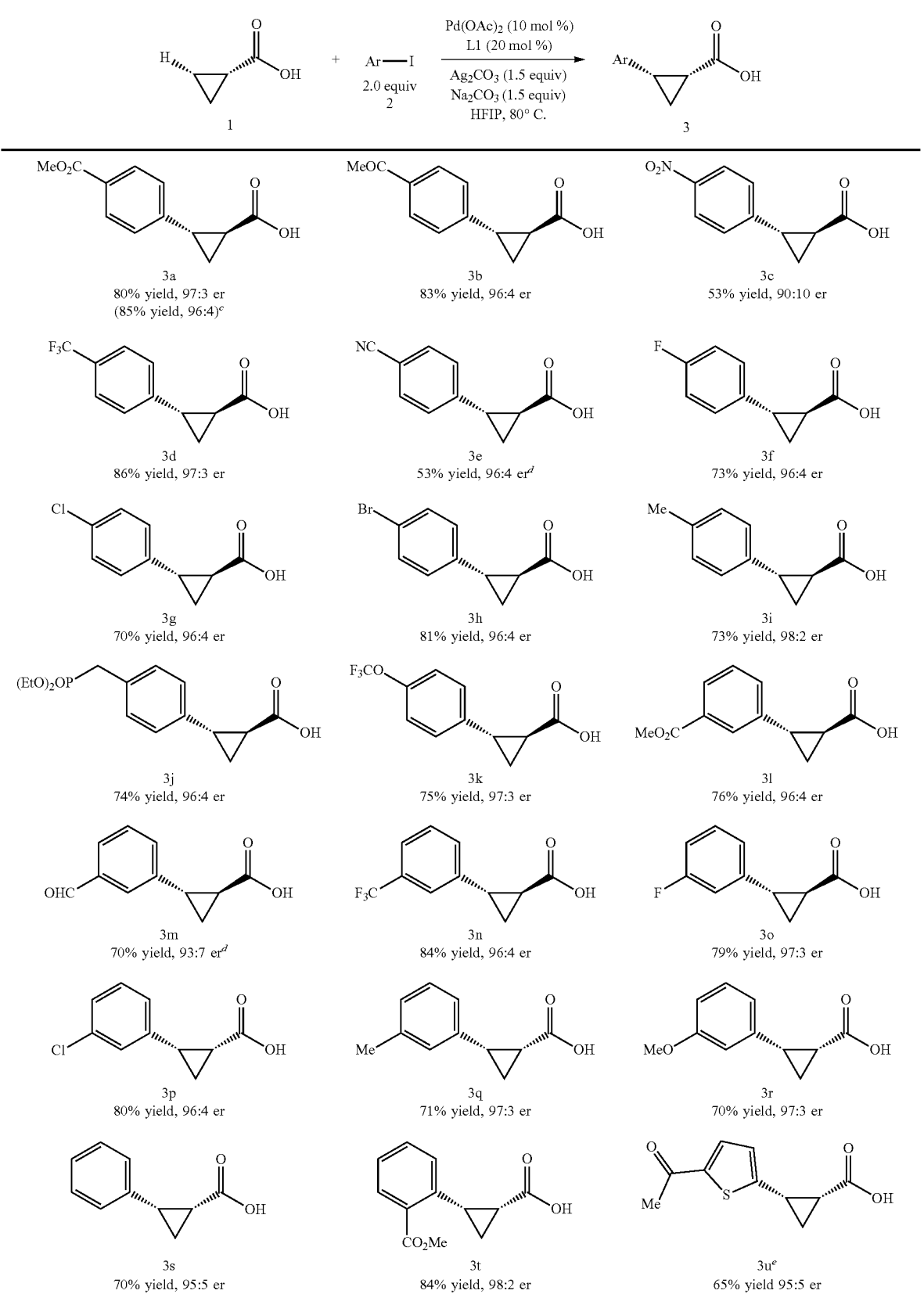

TABLE 2-continued

The Scope of Aryl Iodides for Enantioselective Arylation of Cyclopropanocarboxylic Acid[a,b]

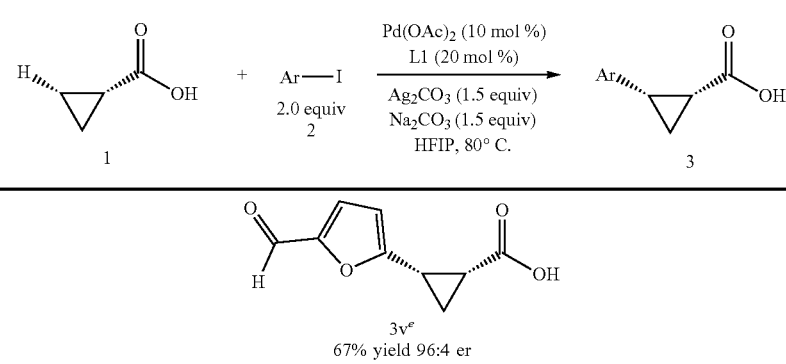

3v[e]
67% yield 96:4 er

[a]Conditions: 1 (0.2 mmol), 2 (2.0 equiv), Pd(OAc)$_2$ (10 mol %), L1 (20 mol %), Ag$_2$CO$_3$ (1.5 equiv), Na$_2$CO$_3$ (1.5 equiv), HFIP (0.25 mL), 80° C., air, 16 h.
[b]Isolated yields.
[c]Conditions 2a (0.2 mmol), 1 (2.0 equiv), Pd(OAc)$_2$ (10 mol %), L1 (20 mol %), Ag$_2$CO$_3$ (1.0 equiv), Na$_2$CO$_3$ (1.5 equiv), HFIP (0.25 mL), 80° C., air, 16 h.
[d]Using AgOAc (3.0 equiv) instead of Ag$_2$CO$_3$ (1.5 equiv), NaHCO3 (1.5 equiv) instead of Na$_2$CO$_3$ (1.5 equiv).
[e]Using 2 (1.5 equiv).

TABLE 3

Enantioselective Arylation of Substituted Cyclopropanecarboxylic Acid[a,b]

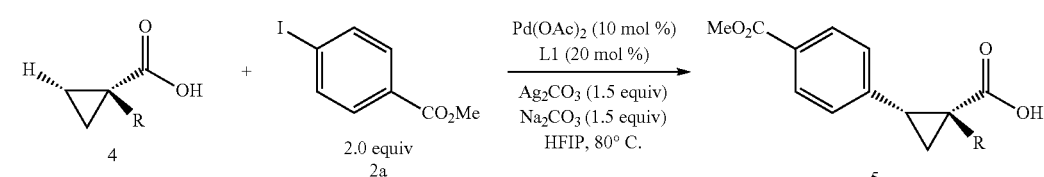

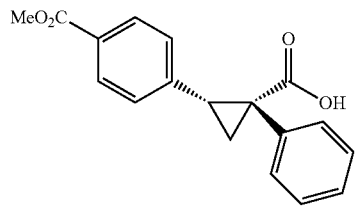 [SMILES: COC(=O)c1ccc([C@H]2C[C@]2(C(=O)O)c2ccccc2)cc1]

5a
76% yield, 98:2 er

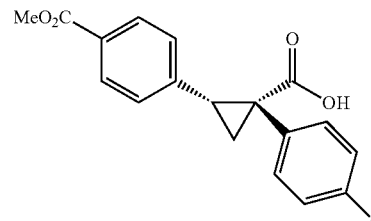

5b
80% yield, 99:1 er

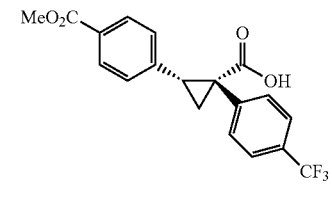

5c
90% yield, 98:2 er

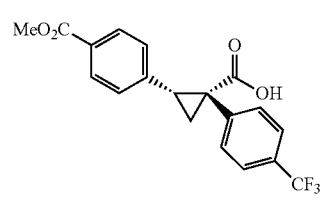 [SMILES: COC(=O)c1ccc([C@H]2C[C@]2(C(=O)O)c2ccc(C(F)(F)F)cc2)cc1]

5d
85% yield, 99:1 er

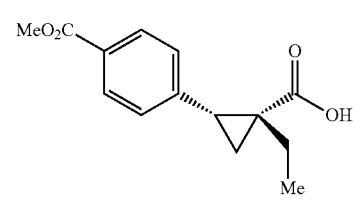 [SMILES: CC[C@@]1(C(=O)O)C[C@@H]1c1ccc(C(=O)OC)cc1]

5e
71% yield, 95:5 er[c]

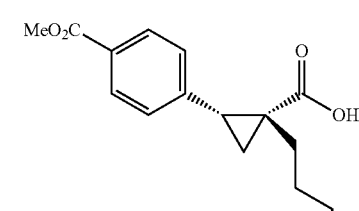

5f
76% yield, 95:5 er[c]

TABLE 3-continued

Enantioselective Arylation of Substituted Cyclopropanecarboxylic Acid[a,b]

5g
58% yield, 96:4 er[c]

5h
80% yield, 96:4 er[c]

5i
63% yield, 96:4 er[d]

5j
64% yield, 96:4 er[d]

5k
65% yield, 96:4 er 5l
71% yield, 98:2 er

[a]Conditions: 4 (0.2 mmol), 2a (2.0 equiv), Pd(OAc)$_2$ (10 mol %), L1 (20 mol %), Ag$_2$CO$_3$ (1.5 equiv), Na$_2$CO$_3$ (1.5 equiv), HFIP (0.25 mL), 80° C., air, 16 h.
[b]Isolated yields.
[c]60° C.
[d]Using AgOAc (3.0 equiv) instead of Ag$_2$CO$_3$ (1.5 equiv), NaHCO3 (1.5 equiv) instead of Na$_2$CO$_3$ (1.5 equiv), 60° C.

The performance of this new chiral ligand was further tested in the enantioselective arylation of phthalyl-protected 2-aminoisobutyric acids via desymmetrization of the dimethyl (Table 4). Such reaction could provide a simple avenue for the synthesis of diverse chiral α-amino acids.

TABLE 4

Enantioselective Arylation of 2-aminoisobutyric Acid[a,b]

7a
65% yield, 86:14 er 7b
67% yield, 87:13 er[c]

7c
60% yield, 89:11 er[c]

TABLE 4-continued

Enantioselective Arylation of 2-aminoisobutyric Acid[a,b]

| 7d | 7e | 7f |
|---|---|---|
| 60% yield, 91:9 er[c] | 65% yield, 92:8 er[c] | 65% yield, 93:7 er[c] |

| 7g | 7h |
|---|---|
| 67% yield, 86:14 er | 65% yield, 92:8 er[c] |

[a]Conditions: 1 (0.1 mmol), 7 (2.5 equiv), Pd(OAc)$_2$ (10 mol %), L1 (20 mol %), AgOAc (3.0 equiv), NaHCO3 (1.5 equiv), HFIP, 80° C., air, 24 h.
[b]Isolated yields.
[c]Isolated as the corresponding methyl ester.

While aryl iodides bearing different substituents gave similar yields of products, the enantioselectivity varied. Electron-neutral group-substituted aryl iodides gave good enantioselectivity, aryl iodides containing electron-withdrawing groups (7a, 7b, and 7g): provided lower er. Since aryl iodides are not involved in the enantio-determining C—H activation step, it is possible that one of the chiral palladacycle intermediates from this particular substrate is less reactive in the oxidation addition step with aryl iodide, thereby contributing to the enantioselectivity partially. A further extensive mechanistic study will be conducted to rationalize this observation.

To further demonstrate the utility of this new methodology, a late-stage C—H functionalization of a promising drug candidate on neurological disorders, ltanapraced,[13] was performed. The reaction proceeded smoothly, and the modified molecule was obtained in high yield and with excellent enantioselectivity (eq 1).

In summary, we have developed a new class of chiral acetyl-protected aminoethyl amine ligands which enable the enantioselective C—H activation of free carboxylic acids without using exogenous directing groups. Enantioselective C—H arylation of simple cyclopropanecarboxylic acid and phthalyl-protected 2-aminoisobutyric acid provides a new synthetic disconnection for asymmetric synthesis of diverse chiral carboxylic acids, The successful design of this new ligand to match the weakly coordinating carboxylic acid for stereocontrol offers a framework for understanding the chiral induction in sp$^3$ C—H activation.

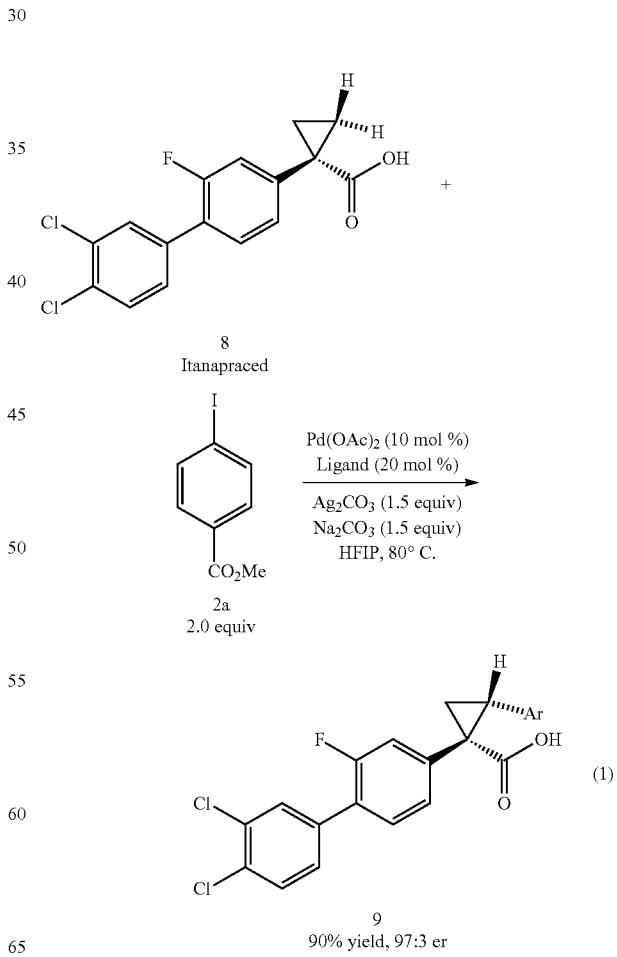

EXAMPLES

Carboxylic acids were obtained from the commercial sources or synthesized following literature procedures. Alkyl iodides were obtained from the commercial sources. Solvents were obtained from Sigma-Aldrich, Oakwood, and Acros and used directly without further purification. Analytical thin layer chromatography was performed on 0.25 mm silica gel 60-F254. Visualization was carried out with UV light and Bromocresol Green Stain. $^1$H NMR was recorded on Bruker DRX-600 instrument (600 MHz). Chemical shifts were quoted in parts per million (ppm) referenced to the literature values of tetramethylsilane. The following abbreviations (or combinations thereof) were used to explain multiplicities: s=singlet, d=doublet, t=triplet, q=quartet, p=pentet, m=multiplet, br=broad. Coupling constants, J, were reported in Hertz unit (Hz). $^{13}$C NMR spectra were recorded on Bruker DRX-600 instrument (150 MHz), and were fully decoupled by broad band proton decoupling. Chemical shifts were reported in ppm referenced to either the center line of a triplet at 77.0 ppm of chloroform-d or the center line of a multiplet at 29.84 ppm of acetone-o$^6$. High-resolution mass spectra (HRMS) were recorded on an Agilent Mass spectrometer using ESI-TOF (electrospray ionization-time of flight). Enantiomeric ratios (er) were determined on an Agilent SFC system or Waters SSC system using commercially available chiral columns.

Standard abbreviations for chemical groups such as are well known in the art are used; e.g., Me=methyl, Et=ethyl, i-Pr=isopropyl, Bu=butyl, t-Bu=tert-butyl, Ph=phenyl, Bn=benzyl, Ac=acetyl, Bz=benzoyl, and the like.

Aryl groups are cyclic aromatic hydrocarbons that may or may not include heteroatoms in the ring. An aromatic compound, as is well-known in the art, is a multiply-unsaturated cyclic system that contains 4n+2 π electrons where n is an integer. Examples include phenyl, naphthyl, furyl, thienyl, pyridyl, and similar groups. Aryl groups can be unsubstituted; or can be substituted with alkyl, halo, haloalkyl, alkoxyl, haloalkoxyl, carboxaldehyde, carboxyester, and similar substituents.

An aryl iodide, as the term is used herein, refers to a compound comprising one or more aryl rings, wherein an iodo group is covalently bound to an aryl ring.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-ingold-Prolog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated as having an (R) absolute configuration, and if the descending rank of the other groups proceeds counterclockwise, the molecule is designated as having an (S) absolute configuration. In the example in the Scheme below, the Cahn-ingold-Prelog ranking is A>B>C>D. The lowest ranking atom, D is oriented away from the viewer. The solid wedge indicates that the atom bonded thereby projects toward the viewer out of the plane of the paper, and a dashed wedge indicates that the atom bonded thereby projects away from the viewer out of the plan of the paper, i.e., the plane "of the paper" being defined by atoms A, C, and the chiral carbon atom for the (R) configuration shown below.

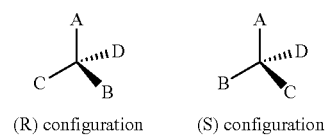

(R) configuration    (S) configuration

A carbon atom bearing the A-D atoms as shown above is known as a "chiral" carbon atom, and the position of such a carbon atom in a molecule is termed a "chiral center." Compounds of the invention may contain more than one chiral center, and the configuration at each chiral center is described in the same fashion.

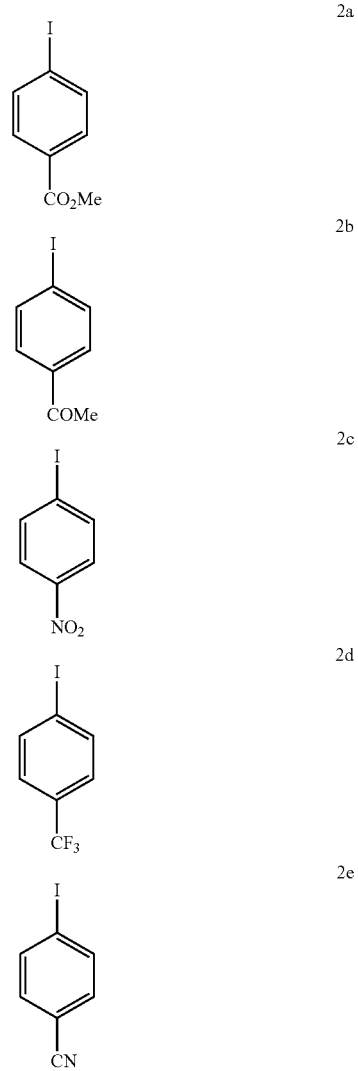

-continued
2f 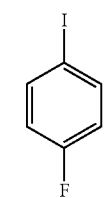
2g 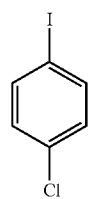
2h 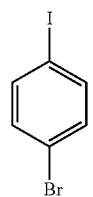
2i 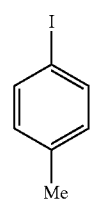
2j 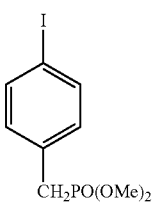
2k 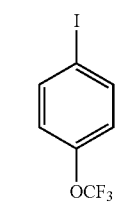
2l 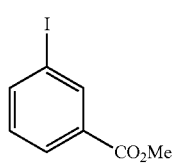
2m 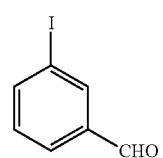
-continued
2n 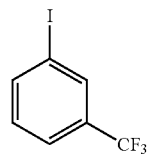
2o 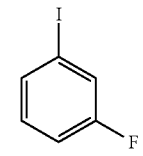
2p 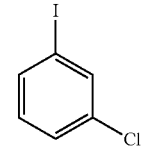
2q 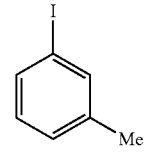
2r 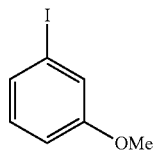
2s 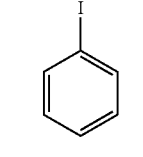
2t 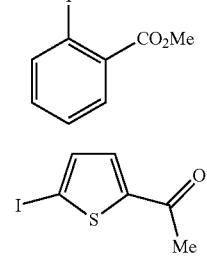
2u 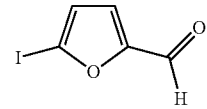
2v
α-Substituted Cyclopropanecarboxylic Acids
4a 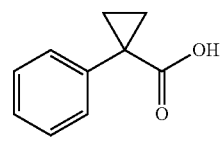

-continued

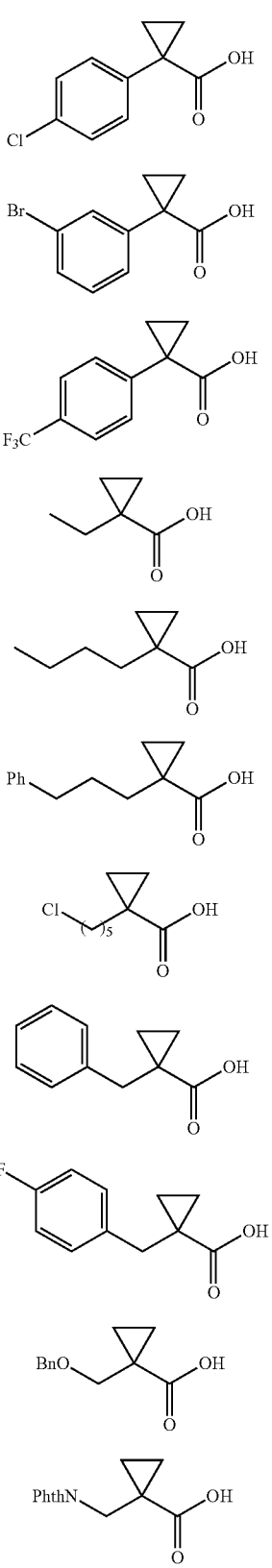

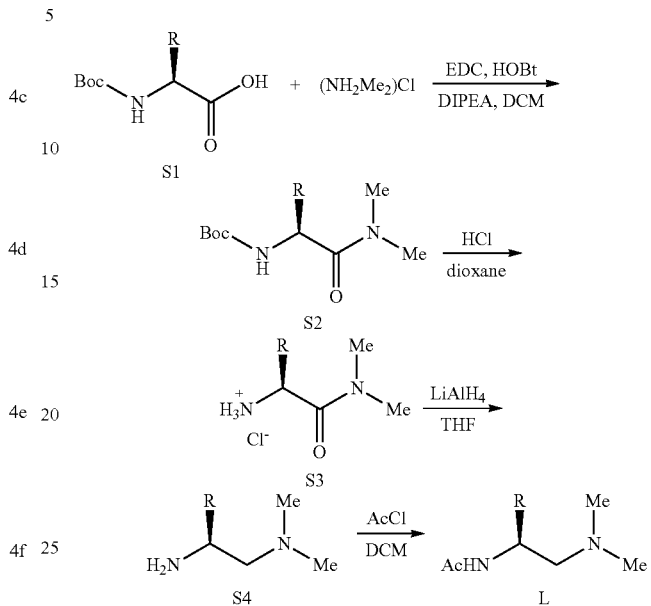

protected amino acids. L19 was synthesized from Boc-protected (2,6-diphenylphenyl)alanine which was synthesized following reported procedure[1]

The corresponding Boc-protected amino acid (S1) (5 mmol), dimethylammonium chloride (11 mmol, 0.90 g) and benzotriazol-1-ol hydrate (HOBt) (5 mmol, 0.77 g) were added to a round bottom flask equipped with a magnetic stir bar. The solid mixture was dissolved in DCM (50 mL), and 1-ethyl-(3-(3-dimethylamino)propyl)-carbodiimide hydrochloride (EDC) (6 mmol. 1.15 g) was added at 0° C. The resulting solution was stirred at 0° C. as N-ethyl-N,N-diisopropylamind (DIPEA) (12 mmol, 1.55 g, 2.09 ml) was added slowly. The reaction solution was allowed to warm to r.t. and stirred for about 3 h. after which the solution was poured into a separatory funnel, diluted to 150 mL with additional DCM, and washed with approximately 25 mL of 10% w/w aqueous citric acid. The organic layer was separated and subsequently washed with 25 mL each of saturated aqueous $NaHCO_3$ and brine. The organics were dried over anhydrous $Na_2SO_4$, filtered, and concentrated in vacuo to provide corresponding amide (S2) which could be directly used in the next step without further purification.

To the Boc-protected amino amide (S2) was added 4 N HCl/dioxane solution (5 ml). The resulting solution was stirred at room temperature for 2 h. Then, the volatile components were evaporated in vacuo, and the residue was subsequently used in the following reduction step.

To a solution of S3 in THF (10 ml) was added a solution of $LiAlH_4$ in THF (2.4 M, 3.12 ml. 7.5 mmol) dropwise under $N_2$ at 0° C. Then, the mixture was heated to reflux for 12 h. before being cooled down and diluted with ether. The mixture was cooled to 0° C., and 0.28 ml of water was added slowly followed by 15% w/w NaOH aqueous solution (0.28 ml) and water (0.84 ml). The resulting suspension was then warmed to room temperature and stirred for 15 min before $MgSO_4$ was added. The mixture was stirred for additional 15 min before filtration. The filtrate was collected, and the solvent was removed in vacua to provide diamine compound (S4) which could be used in next step without purification.

To a solution of the synthesized diamine compound (S4) in DCM (10 ml) was added acetyl chloride (10 mmol, 0.78

Preparation of Ligands
Ligand L1-18, L20-21 were synthesized using the following procedure from corresponding commercially available Bocg, 0.71 ml) at 0° C. Then the solution was stirred at room temperature for 2 h. The volatile components were evaporated in vacuo, and the residue was dissolved in 10 ml of water. The resulting solution was extracted with ether (10 ml x3), then the aqueous phase was alkalized with 15% w/w NaOH aqueous solution until pH>13. The alkalized Mixture was extracted with ether (10 ml x3), and the organic layers were concentrated to provide the desired APAA Ligand. The compounds were usually pure enough for subsequent Pd-catalyzed C—H functionalization. Further purification could be conducted by recrystaliization or reversed phase flash column.

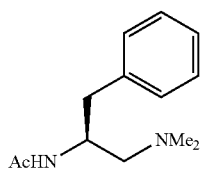

(S)-N-(1-(dimethylamino)-3-phenylpropan-2-yl)acetamide (L1)

L1 was synthesized following the standard procedure, and could be purified by recrystallized to provide white solid. $^1$H NMR (600 MHz, CDCl$_3$) δ 7.29 (t, J=7.5 Hz, 2H) 7.22 (tt, J=6.9, 1.5 Hz, 1H), 7.18 (d, J=7.2 Hz, 2H), 5.56 (br-d, J=8.4 Hz, 1H, N—H) 4.22-4.16 (m, 1H), 2.97 (dd, J=13.8, 4.8 Hz, 1H), 2.84 (dd, J=13.8, 6.6 Hz, 1H), 2.29 (dd, J=12.6, 9.0 Hz, 1H), 2.19 (s, 6H), 2.16 (dd, J=12.3, 5.7 Hz, 1H), 1.96 (s, 3H); $^{13}$C NMR (150 MHz, CDCl$_3$) δ 170.27, 137.85, 129.65, 128.45, 126.52, 61.56, 48.28, 45.70, 38.59, 23.72.

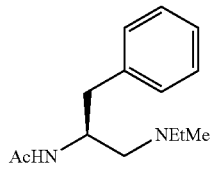

(S)-N-(1-(ethyl(methyl)amino)-3-phenylpropan-2-yl)acetamide (L2)

The corresponding Boc-protected amino amide was synthesized using ethylmethylamine (6 mmol). Then, following standard procedure, L2 was obtain as pale-yellow solid, which was used without further purification. $^1$H NMR (600 MHz, CDCl$_3$) δ 7.29 (t, J=7.8 Hz, 2H), 7.23-7.18 (m, 3H), 5.76 (br, 1H, N—H), 4.22-4.17 (m, 1H), 2.98 (dd, J=13.8, 5.4 Hz, 1H), 2.84 (dd, J=13.6, 6.9 Hz, 1H), 2.48-2.43 (dq, J=12.6, 7.2 Hz, 1H), 2.41-2.36 (m, 2H), 2.26 (dd, J=12.6, 6.0 Hz, 1H), 2.19 (s, 3H), 1.96 (s, 3H), 1.00 (t, J=7,2 Hz, 3H); $^3$C NMR (150 MHz, CDCl$_3$) δ 170.29, 137.99, 129.78, 128.45, 126.50, 59.02, 51.53, 48.24, 41.72, 38.72, 23.70, 12.00.

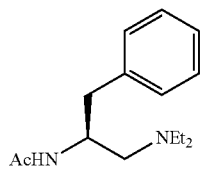

(S)-N-(1-(diethylamino)-3-phenylpropan-2-yl)acetamide. (L3)

The corresponding Boc-protected amino amide was synthesized according to reported procedure.[2] Then, following standard procedure, L3 was obtain as pale-yellow solid, which was used without further purification. $^1$H NMR (600 MHz, CDCl$_3$) δ 7.29 (t, J=7.5 Hz, 2H), 7.22-7.19 (m, 3H), 5.7s (br-d, J=3.6 Hz, 1H, N—H), 4.16-4.11 (m, 1H), 2.96 (dd, J=13.8, 5.4 Hz, 1H), 2.86 (dd, J=13.8, 6.6 Hz, 1H), 2,56-2.45 (m, 4H), 2.40 (dd, J=12.3, 8.1 Hz, 1H), 2.36 (dd, J=12.3 6.3 Hz, 1H), 1.94 (s, 3H), 0.95 (t, J=7.2 Hz, 6H); $^{13}$C NMR (150 MHz, CDCl$_3$) δ 170.24, 138.26, 1.29.65, 128.39, 126.39, 55.43, 48.70, 47.03, 38.74, 23.68, 11.68.

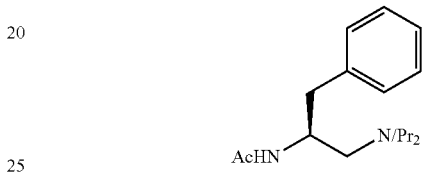

(S)-N-(1-(diisopropylamino)-3-phenylpropan-2-yl)acetamide (L4)

The corresponding Boc-protected amino amide was synthesized according to reported procedure.[3] Then, following standard procedure, L4 was obtain as pale-yellow solid, which was used without further purification. $^1$H NMR (600 MHz, CDCl3) δ 7.29-7.26 (m, 2H), 7.21-7.18 (m, 3H), 5.68 (br-d, J=4.8 Hz, 1H, N—H), 4.04-3.98 (m, 1H), 3.00-2.94 (m 3H), 2.87 (dd, J=8.1, 6.3 Hz, 1H), 2,46 (dd, J=13.2, 6.6 Hz, 1H), 2.41 (dd, J=13.4, 8.7 Hz, 1H), 1.93 (s, 3H), 0.96 (d, J=7.2 Hz, 6H), 0.95 (d, J=6.6 Hz, 6H); $^{13}$C NMR (150 MHz, CDCl$_3$) δ 170.37, 138.89, 129.56; 128.37, 126.30, 49.38, 47.93, 47.56, 38.91, 23.67, 21.68; 20.31,

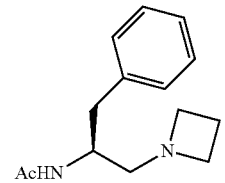 [SMILES: CC(=O)N[C@@H](Cc1ccccc1)CN1CCC1]

p (S)-N-(1-(azetidin-1-yl)-3-phenylpropan-2-yl)acotamide (L5)

The corresponding Boc-protected amino amide was synthesized using azetidine (20 mmol). Then, following standard procedure, L5 was obtain as pale-yellow solid, which was used without further purification. 1H NMR (600 MHz, CDCl$_3$) δ 7.30-7.27 (m, 2H), 7.21 (tt, J=7.5, 1.4 Hz, 1H), 7.19-7.17 (m, 2H), 5.69 (br-d, J=6.0 Hz, 1H, N—H), 4.08-4.02 (m, 1H), 3.24-3.19 m, 4H), 2.89 (dd, J=13.8, 6.0 Hz, 1H), 2.78 (dd, J=13.8, 7.2 Hz, 1H), 2.42 (ABq-d, J$_{AB}$=12.4 Hz, Δδ=0.02, J$_3$=6.9, 5.4 Hz, 2H), 2.06 (p, J=7.2 Hz, 2H), 1.95 (s, 3H); $^{13}$C NMR (150 MHz, CDCl$_3$) δ169.93, 138.10, 129.62, 128.48, 126.50, 61.45, 56.17, 49.13, 38,65, 23.72, 18.06.

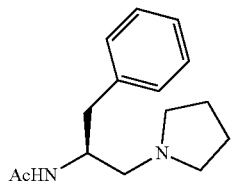 [SMILES: CC(=O)N[C@@H](Cc1ccccc1)CN1CCCC1]

(S)-N-(1-phenyl-3-(pyrrolidin-1-yl)propan-2-yl)acetamide (L6)

The corresponding Boc-protected amino amide was synthesized according to reported procedure.[4] Then, following standard procedure, L6 was obtain as pale-yellow solid, which was used without further purification. $^1$H NMR (600 MHz, CDCl$_3$) δ 7.29 (t, J=7.5 Hz, 2H), 7.23-7.18 (m, 3H), 5.63 (br-d, J=4.2 Hz, 1H, N—H), 4.23-4.17 (m, 1H), 2.97 (dd, J=. 13.5, 5.1 Hz, 1H), 2.85 (dd, J=13.5, 6.9 Hz, 1H), 2.53-2.50 (m, 3H), 2.47-2.43 (m, 2H), 2.36 (dd, J=12.6, 6.0 Hz, 1H), 1.98 (s, 3H), 1.75-1.72 (m, 4H); $^{13}$C NMR (150 MHz, CDCl$_3$) δ170.14, 138.02, 129.85, 128.42, 126.47, 58.11, 54.36, 49.46, 38.75, 23.77. 23.72.

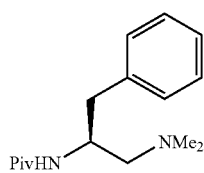

(S)-N-(1-(dimethylamino)-3-phenylpropan-2-yl)pivalamide (L7)

The corresponding diamine S3 was acylated with pivaloyl chloride (10 mmol, 1.20 g, 11.22 ml) to provide L7 as pale-yellow solid, which was used without further purification. $^1$H NMR (600 MHz, CDCl$_3$) δ 7.28 (t, J=7.5 Hz, 2H), 7.21 (tt, J=7.5, 1.5 Hz, 1H), 7.19-7.15 (m, 2H), 5.83 (br-d, J=5.4 Hz, 1H, N—H), 4.14-4.09 (m, 1H), 2.97 (dd, J=13.5, 5.1 Hz, 1H), 2.88 (dd, J=13.2, 6.6 Hz, 1H), 2.29 (dd, J=12.3, 8.1 Hz, 1H), 2.21-2.18 (m, 7H), 1.14 (s, 9H); $^{13}$C NMR (150 MHz, CDCl$_3$) δ 178.63, 138.04, 129.91, 126.37, 126.46, 61.47, 48.14, 45.69, 38.89, 38.43, 27.67.

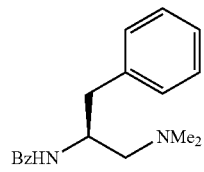

(S)-N-(1-(dimethylamino3-phenylpropan-2-yl)benzamide (L8)

The corresponding diamine S3 was acylated with benzoyl chloride (7.5 mmol, 1.05 g, 0.87 ml) to provide L7 as pale-yellow solid, which was used without further purification. $^1$H NMR (600 MHz, CDCl$_3$) δ 7.74-7.73 (m, 2H), 7.48 (tt, J=7.5, 1.5 Hz, 1H), 7.42 (t, J=7.5 Hz, 2H), 7.31-7.29 (m, 2H), 7.24-7.22 (m, 3H), 6.37 (br-d, J=4.8 1Hz, N—H), 4.37-4.32 (m, 1H), 3.14 (dd, J=13.5, 4,5 Hz, 1H), 2.99 (dd, J=13.5, 6.9 Hz, 1H), 2.42 (dd, J=12.0, 9.0 Hz, 1H), 2.27 (dd, J=12.6, 6.0 Hz, 1H), 2.22 (s, 6H); $^{13}$C NMR (150 MHz, CDCl$_3$) δ167.69, 137,87, 135.05, 131.50, 129.99, 128.67, 128.49, 127.07, 126.57, 61.36, 48.71, 45.72, 38.49.

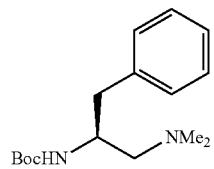

Teri-butyl (S)-(1,-(dimethylamino)-3-phenylpropan-2-yl)carbarnate (L9)

The corresponding diamine 63 was acylated with Boc$_2$O (7.5 mmol, 1.64 g) to provide L9 as white solid, which was used without further purification. $^1$H NMR (600 MHz, CDCl$_3$) δ 7.28 (t, J=7.5 Hz, 2H), 7.22-7.18 (m, 3H), 4.67 (br, 1H, N—H), 3.87 (br, 1H), 2.94-2.92 (br-m, 1H), 2.83 (dd, J=13.5, 6.3 Hz, 1H), 2.28-2.25 (br-m, 1H), 2.21 (s, 6H), 2.17 (dd, J=12.3, 6.3 Hz, 1H), 1.42 (s, 9H); $^{13}$C NMR (150 MHz, CDCl$_3$,) δ 155.87, 138,10 129.84, 128.39, 126.38, 79.30, 61.93, 49.49, 45.69, 39.02, 28.54.

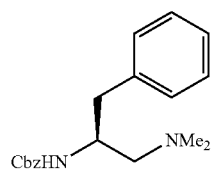 [SMILES: CN(C)C[C@H](Cc1ccccc1)NC(=O)OCc1ccccc1]

Benzyl (S)-(1-(dimethylamino)-3-phenylpropan-2-yl)carbamate (L10)

The corresponding diamine S3 was acylated with benzyl chloroformate (7.5 mmol, 1.28 g) to provide L10 as colorless oil, which was used without further purification. $^1$H NMR (600 MHz, CDCl$_3$) δ 7.37-7.30 (m, 5H), 7.27 (t, J=7.2 Hz, 2H), 7.21 (tt, J=7.5, 1.5 Hz, 2H), 7.16 (d, J=7.2 Hz, 2H), 5.12 (d, 12.0 Hz, 1H), 6.06 (d, J=12.0 Hz, 1H), 4.95 (br, 1H, N—H), 3.94-3.92 (br-m, 1H), 2.99-2.96 (br-m, 1H), 2.84 (dd, J=13.8, 6,6 Hz, 1H), 2.27 (dd, J=12.0, 9.0 Hz, 1H), 2.20-2.16 (m, 7H); $^{13}$C NMR (150 MHz, CDCl$_3$) δ 156.33, 137.81, 136.84, 129.82, 128.63, 128.47, 128.16, 12.8.15, 126.51, 66.64, 61.96, 50.10, 45.71, 38.99.

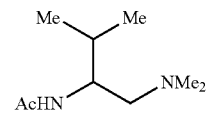 [SMILES: CC(=O)NC(CN(C)C)C(C)C]

(S)-N-(1-(dimethylamino)-3-methylbutan-2-yl)acetarmide (L11)

L11 was synthesized following the standard procedure as colorless oil and used without further purification $^1$H NMR (600 MHz, CDCl$_3$) δ 6.50 (br-d; J=4.8 Hz, 1H, N—H), 3.96-3.91 (m, 1H), 2.36 (dd, J=12.0, 9.6 Hz, 1H), 2.22 (s, 6H), 2.20 (dd, J=12.6, 5.4 Hz, 1H), 2.01 (s, 3H), 1.98-1.93 (m, 1H), 0.90 (d, J=6.6 Hz, 3H), 0.88 (d, J=7.2 Hz, 3H); NMR (150 MHz, CPCl$_3$) δ 170.34, 60.15, 51.78, 45.86, 30.25, 23.78, 18.81, 17.80.

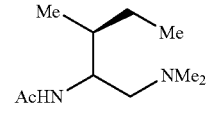 [SMILES: CC[C@H](C)C(CN(C)C)NC(C)=O]

N-((2S,3S)-1-(dimethylamino)-3-methylpentan-2-yl)acetamide (L12)

L12 was synthesized following the standard procedure as colorless oil and used without further purification. $^1$H NMR (600 MHz, CDCl$_3$) δ 5.57 (br-d, J=6.0 Hz, 1N, N—H), 3.98-3.93 (m, 1H), 2.36 (dd, J=12.6; 4.2 Hz, 1H), 2.20 (s, 6H), 2.16 (dd, J=12.3, 5.1 Hz, 1H), 2.00 (s, 3H), 1.80-1.75 (m, 1H), 1.47-1.40 (m, 1H), 1.13-1.05(m, 1H), 0.92 (t, J=7.5 Hz, 3H), 0.86 (d, J=6.6 Hz, 3H); $^{12}$C NMR (150 MHz, CDCl$_3$) δ 170.24, 59.17, 51.21, 45.85, 36.95, 25.49, 23.82, 14.70, 12.17.

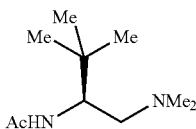 [SMILES: CC(=O)N[C@H](CN(C)C)C(C)(C)C]

(S)-N-(1-(dimethylamino)-3,3-dimethylbutan-2-yl)acetamide (L13)

L13 was synthesized following the standard procedure as white solid and purified by reverse phase column. $^1$H NMR (600 MHz, CDCl$_3$) δ 5.321 (br-d, J=6.0 Hz, 1H, N—H), 3.94 (ddd, J=10.9, 9.8., 3.9 Hz, 1H), 2.32 (dd, J=12.3, 11.1 Hz, 1H), 2.25 (dd, J=12.3, 9.9 Hz, 1H), 2.20 (s, 6H), 2.02 (s, 3H), 0.91 (s, 9H); $^{13}$C, NMR (150 MHz, CDCl$_3$) δ 170.42, 59.55, 54.41, 45.87, 34.61, 26.64, 23.85.

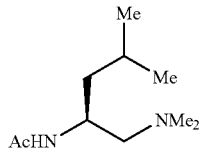 [SMILES: CC(=O)N[C@@H](CC(C)C)CN(C)C]

(S)-N-(1-(dimethylamino)-4-methylpentan-2-yl)acetamide (L14)

L14 was synthesized following the standard procedure as white solid and purified by reverse phase column. $^1$H NMR (600 MHz, CDCl$_3$) δ 5.50 (br-d, J=8.4 Hz, 1H, N—H), 4.10-4.04 (m, 1H), 2.33 (dd, J=12.3, 8.1 Hz, 1H), 2.24 (s, 6H), 2.21 (dd, J=12.6, 6.0 Hz, 1H), 1.98 (s, 3H), 1.68-1.61 (m, 1H), 1.39-1.31 (m, 2H), 0.93 (d, J=6.01 Hz, 3H), 0.92 (d, J=6.6 Hz, 3H); $^{12}$C, NMR (150 MHz, CDCl$_3$) 169.98, 63.86, 46.01, 45.89, 43.35, 25.02, 23.73, 23.24, 22.52,

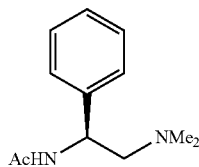 [SMILES: CC(=O)N[C@H](CN(C)C)c1ccccc1]

(S)-N-(2-(dimethylamino)-1-phenylethyl)acetamide (L15)

L15 was synthesized following the standard procedure as pale-yellow solid and used without further purification. $^1$H NMR (600 MHz, CDCl$_3$) δ 7.32 (t, J=7.2 Hz, 2H), 7.28-7.26 (m, 2H), 7.24-7.22 (m, 1H), 6.24 (br, 1H, N—H), 4.88 (dt, J=10.5, 5.4 Hz, 1H), 2.58 (dd, J=12.9, 9.9 Hz, 1H), 2.41 (dd, J=12.6, 5.4 Hz, 1H), 2.24 (s, 6H), 2.04 (s, 3H); $^{13}$C NMR (150 MHz, CDCl$_3$) δ170.17, 141.54, 128.67, 127.35, 126.29, 64.80, 51.92, 45.56, 23.55.

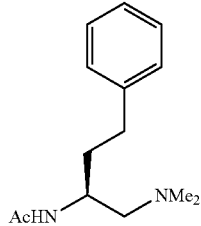 [SMILES: CC(=O)N[C@@H](CCc1ccccc1)CN(C)C]

(S)-N-(1-(dimethylamino)-4-phenylbutan-2-yl) (L16)

L16 was synthesized following the standard procedure as colorless oil and used without further purification. $^1$H NMR (600 MHz, CDC$_{l3}$) δ7.27 (t, J=7.5 Hz, 2H), 7.20-7.16 (m, 3H), 5:54 (br-d, J=6.6 Hz, 1H, N—H), 4.06-4.00 (m, 1H), 2.68-2.65 (m, 2H), 2.38 (dd, J=12.3, 8.7 Hz, 1H), 2.24 (dd, J=12.3, 5.7 Hz, 1H), 2.21 (s, 6H), 1.97 (a, 3H), 1.93-1.88 (m, 1H), 1.81-1.75 (m, 1H); $^{13}$C NMR (150 MHz, CDCl$_3$) δ 1.70.23, 142.08, 128.52, 128.48, 125.99, 63.10, 47.71, 46.00, 35.46, 32.27, 23.73.

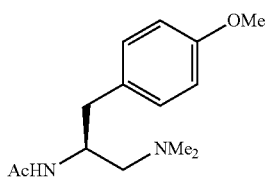 [SMILES: COc1ccc(C[C@@H](CN(C)C)NC(C)=O)cc1]

(S)-N-(1-(dimethylamino)-3-(4-methoxyphenyl)propan-2-yl)acetamide (L17)

L17 was synthesized following the standard procedure as pale-yellow solid and used without further purification. $^1$H NMR (600MHz, CDCl$_3$) δ 7.10-7.08 (m, 2H), 6.84-6.82 (m, 2H), 5.55 (br-d, J=7.2 Hz, 1H, N—H), 4.17-4.11 (m, 1H), 379 (s, 3H), 2.90 (dd, J=13.8, 4.8 Hz, 1H), 2.79 (dd, J=13.8, 6.6 Hz, 1H), 2.27 (dd, J=12.3, 9.3 Hz, 1H), 2.19 (s, 6H), 2.15 (dd, J=12.3, 5.7 Hz, 1H), 1.96(s, 3H); $^{13}$C NMR (150 MHz, CDCl$_3$) δ 170.22, 158.33, 130.78, 129.78, 113.85, 61.52, 55.35, 48.35, 45,71, 37.59, 23,74.

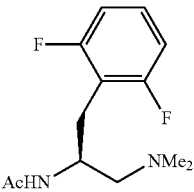

(S)-N-(1-(2,6-difluorophenyl)-3-(dimethylamino)propan-2-yl)acetamide (L18)

L18 was synthesized following the standard procedure as pale-yellow solid and used without further purification. $^1$H NMR (600 MHz, CDCl$_3$) δ 7.19-7.14 (m, 1H), 6.88-6.84 (m, 2H), 5.60 (br-d, J=7.8 Hz, 1H, N—H), 4.29-4.23 (m, 1H), 3.08 (dd, J=13.8, 5.4 Hz, 1H), 2.81 (dd, J=13.8, 7.8 Hz, 1H), 2.40 (dd, J=12.3, 8.7 Hz, 1H), 2.27-2.23 (m, 7H), 1.90 (s, 3H); $^{13}$C NMR (150,MHz,.CDCl$_3$) δ 170.24, 161.94 (dd, J=245, 8 Hz), 128.32 (t, J=10 Hz), 114.14 (t, J=20 Hz), 111.16 (dd, J=20, 4.5 Hz). 62.50, 47.68. 46.78, 26.02, 23.51; $^{19}$F NMR (376 MHz, CDCl3) δ−114.52 (s, 2F).

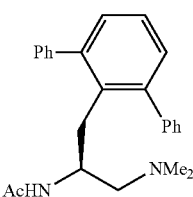 [SMILES: CC(=O)N[C@@H](Cc1c(-c2ccccc2)cccc1-c1ccccc1)CN(C)C]

(S)-N-(1-([1,1':3',1''-terphenyl]-2'-yl)-3-(dimethylamino)propan-2-yl)acetamide (L19)

L19 was synthesized following the standard procedure, and could be purified by recrystallized to provide white solid. $^1$H NMR (600 MHz, CDCl$_3$) δ 7.46-7.41 (m, 8H), 7.38-7.35 (m, 2H), 7.29-7.27 (m, 1H), 7.18 (d, J=7.8 Hz, 2H), 4.60 (br-d, J=9.6 Hz, 1H), 3.77-2.70 (m, 1H), 3.12 (d, J=13.8, 4.2 Hz, 1H), 2.80 (d, J=14.4, 10.8 Hz, 1H), 1.85 (dd, J=12.0, 6.6 Hz, 1H); 1.72 (s, 6H), 1.69 (s, 3H), 1.61 (dd, J=12.0, 7.8 Hz, 1H); $^{13}$C NMR (150 MHz, CDCl$_3$) δ 169.16, 143.49, 142.56, 133.60, 129.92, 129.75, 128.52, 127.18, 126.19, 64.15, 48.22, 45.36, 32.54, 23.57.

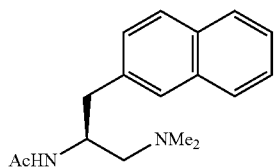

(S)-N-(1-(dimethylamino)-3-(naphthalen-2-yl)propan-2-yl)acetamide (L20)

L20 was synthesized following the standard procedure as pale-yellow solid and used without further purification. $^1$H NMR (600 MHz, CDCl$_3$) δ 7.82-7.87 (m, 3H), 7.62 (s, 1H), 7.47-7.42 (m, 2H), 7.35 (dd, J=8.4, 1.2 Hz, 1H), 5.64 (br-d, J=6.0 Hz, 1H, N—H), 4.30-4.24 (m, 1H), 3.17 (dd, J=13.8, 4.8 Hz, 1H), 2.98 (dd, J=13.8, 6.6 Hz, 1H), 2.33 (dd, J=12.3, 9.3 Hz, 1H), 2.21-2.18 (m, 7H), 1.97 (s, 3H); $^{13}$C NMR (151 MHz, CDCl$_3$) δ 170.35, 135.50, 133.57, 132.35, 128.29, 128.20, 127.99, 127.76, 127.65, 126.15, 125.58, 61.54, 48.43, 45.68, 38.77, 23.74.

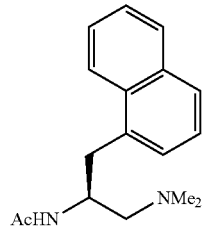 [SMILES: CC(=O)N[C@@H](Cc1cccc2ccccc12)CN(C)C]

(S)-N-(1-(dimethylamino)-3-(naphthalen-1-yl)propan-2-yl)acetamide (L21)

L21 was synthesized following the standard procedure as pale-yellow solid and used without further purification. $^1$H NMR (600 MHz, CDCl$_3$) δ 8.45 (d, J=8.4 Hz, 1H), 7.84 (d, J=8.4 Hz, 1H), 7.75 (d, J=7.8 Hz, 1H), 7.56 (ddd, J=8.4, 6.9, 1.5 Hz, 1H), 7.50-7.46 (m, 1H), 7.38, (dd, J=8.1, 6.9 Hz, 1H), 7.29 (d, J=6.6 Hz, 1H), 5.82 (br-d, J=6.0 Hz, 1H), 4.31-4.26 (m, 1H), 3.74 (dd, J=13.9, 4 8 Hz, 1H), 3.04 (dd, J=13.8, 8.4 Hz, 1H), 2.40 (dd, J=12.3, 9.3 Hz, 1H), 2.17-2.14 (m, 7H), 1.98 (s, 3H); $^{13}$C NMR (150 MHz, CDCl$_3$) δ 170.73, 134.43, 134.02, 132.73, 128.64, 127.87, 127.43, 126.32, 125.83, 125.28, 124.88, 61.79, 48.14, 45.60, 36.55, 23.74.

Preparation of Substrates.

1, 4a, and 4b were purchased from commercial sources. 4c and 4d were synthesized from the reported procedure.[2]

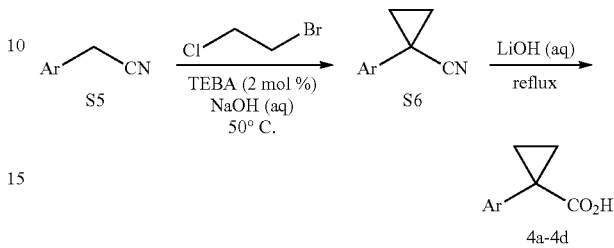

To a flask charged with a magnetic stir bar and the arylacetonitrile (S5) (6.6 mmol) was added 1-bromo-2-chloroethane (9.9 mmol), benzyltriethylammonium chloride (0.132 mmol), and 50% aqueous sodium hydroxide (39.6 mmol). The resulting solution was stirred at 50° C. under a reflux condenser and ambient atmosphere for 12 h. The solution was poured into water and extracted with dichloromethane twice. The combined organic extracts were washed with 3 N HCl, saturated aqueous. NaHCO$_3$, and brine. The organic layer was dried over anhydrous Na$_2$SO$_4$, filtered and concentrated in vacuo to give the desired 1-aryl-1-cyanocyclopropane product (S6), typically in sufficient purity to be carried forward without further purification to the next step.

To a flask containing 1-aryl-1-cyanocyclopropane (S6) (6.6 mmol) was added a slurry of lithium hydroxide in water (4.0 M, 212 mmol). The flask was heated to reflux and stirred for 24 h. The reaction was cooled to room temperature, then 2 N HCl was added until pH<1. The solution was extracted with ethyl acetate for three times. The combined ethyl acetate extracts were dried over anhydrous Na$_2$SO$_4$, filtered and concentrated in vacua to give the desired 1-aryl-cyclopropariecarboxylic acid product, typically in sufficient purity to be carried forward to Pd-catalyzed reaction without further purification. The spectra of 4c[6] and 4d[7] have been reported in the literature.

4e-4j were synthesized following the previously reported procedure.[5]

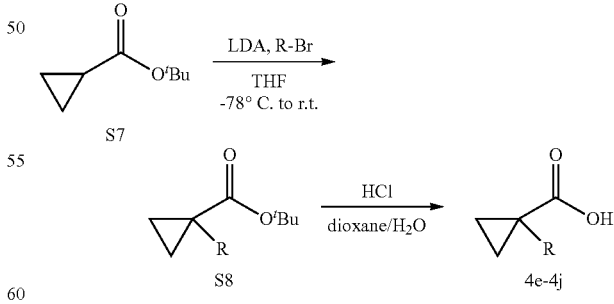

A freshly prepared solution of lithium diisopropylamide (12 mmol) in THF/hexanes (30 ml) was cooled to −78° C. A solution of tert-butyl cyclopropanecarboxylate (S7) (10 mmol, 1.42 g) THF (10 ml) was added slowly dropwise over 5 Min. The resulting solution was stirred at −78° C. for 2 h. A solution of the alkyl bromide (30 mmol) in THF (10 ml)

was added slowly dropwise over 10 min. The solution was then allowed to warm to room temperature slowly and stirred overnight. Then, the reaction was quenched by addition of saturated aqueous ammonium chloride. The aqueous phase was extracted twice with diethyl ether. The combined organic phases were washed with brine, dried over sodium sulfate, filtered and concentrated in vacuo. The product (S8) was then purified by silica gel flash chromatography (typically 3% v/v ether in hexanes).

10 ml of 4 N HCl in dioxane was added to the previously prepared tert-butyl ester, and 0.5 ml of water was added to the solution (warning: exothermic process). The mixture was stirred at room temperature for 24 h. The reaction solution was concentrated in vacuo, and then the residue was dissolved in methanol. The resulting solution was dried over sodium sulfate, filtered and concentrated to give the desired free acid, typically in sufficient purity to be carried forward to Pd-catalyzed reaction without further purification. The spectra of 4e[8] and 4l[9] have been reported.

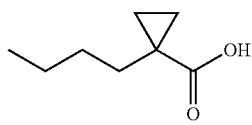

1-Butylcyclopropene-1-carboxylic acid (4f)
$^1$H NMR (600 MHz, CDCl$_3$) δ 1.52-1.49 (m, 2H), 1.47-1.42 (m 2H), 1.30 (q, J=7.4 Hz, 2H). 1.27-1.25 (m, 2H), 0.89 (t, J=7.2, 3H), 0.76-0.74 (m, 2H); $^{13}$C NMR (150 MHz, CDCl$_3$) δ 182.13, 33.46, 29.88, 23.44, 23.02, 16.59, 14.16.

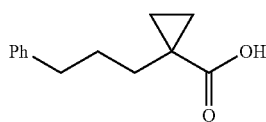

1-(3-Phenylpropyl)cyclopropane-1-1-carboxylic acid (4g)
$^1$H NMR (600 MHz, CDCl$_3$) δ 7,28-7.25 (m, 2H), 7.18-7.16 (m, 3H), 2.61 (t, J=7.8 Hz, 2H), 1.84-1.78 (m, 2H), 1.57-1.54 (m, 2H), 1.27-1.26 (m, 2H), 0.74-0.73 (m, 2H); $^{13}$C NMR (150 MHz, CDCl$_3$) δ 182.57, 142.46, 128.49, 128.42, 125.84, 36.12, 33.41, 29.34, 28.22, 23.41, 16,70.

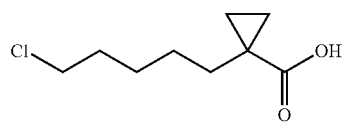 [SMILES: O=C(O)C1(CCCCCCl)CC1]

1-(5-Chloropentyl)cyclopropane-1 -carboxylic acid (4h)
$^1$H NMR (600 MHz, CDCl$_3$) Y 3.53 (t, J=6.6 Hz, 2H), 1.78 (p, J=7.2 Hz, 2H), 1.53-1.49 (m, 4H), 1.45-1.40 (m, 2H), 1.29-1.27 (m, 2H), 0.77-0.75 (m, 2H); $^{13}$C NMR (150 MHz, CDCl$_3$) Y 182.27, 45.20, 33.61, 32.63, 27.13, 26.98, 23.38, 16.69,

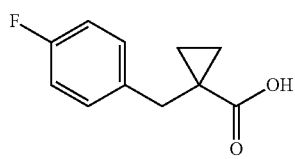 [SMILES: O=C(O)C1(Cc2ccc(F)cc2)CC1]

1-(4-Fluorobenzl)cyclopropane-1-carboxylic acid (4j)
$^1$H NMR (600 MHz, CDCl$_3$) δ 7.21-7.18 (m, 2H), 6.97-6.93 (m, 2H), 2.92 (s, 2H), 1.36-1.35 (m, 2H), 0.88-0.86 (m, 2H); $^{13}$C NMR (150 MHz, CDCl$_3$) δ 181.94, 161.69 (d, J=243 Hz), 134.99 (d, J=3 Hz), 130.70 (d, J=8 Hz), 115.08 (d, J=21 Hz), 37.26, 23.89, 16.22; $^{19}$F NMR (376 MHz, CDCl$_3$) δ -117.33 (s, 1F),

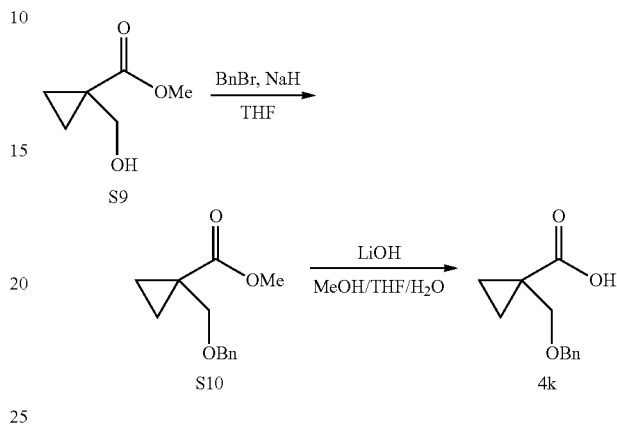

To a stirred suspension of 60% sodium hydride (NaH) in mineral oil (0.120 g, 30.0 mmol) in anhydrous THF (10 mL), cooled in an ice bath, was added methyl 1-hydroxymethyl cyclopropanecarboxylic acid (10.0 mmol, 1.30 g). The resultant suspension was stirred for 20 min at room temperature. Benzyl bromide (10.0 mmol, 1.71 g, 1.21 ml) was slowly added at 0° C., and the reaction was stirred at room temperature overnight. The reaction suspension was chilled in an ice bath, and the excess NaH was quenched with water (15 mL). The reaction mixture was extracted with ethyl acetate (3x25 mL). The combined organics were dried over MgSO$_4$, filtered, and concentrated. The residue was purified by flash chromatography (silica gel, 10% ethyl acetate in hexanes) to deliver S310.

S10 was dissolver in the mixture of THF (32 ml), water (32 ml) and MeOH (16 ml) and then LiOH.H$_2$O (30 mmol, 0.126 g) was added. The resulting mixture was stirred overnight and then was acidified by adding 3 M HCl solution. The mixture was extracted with ethyl acetate. Then combined organic layers were dried over Na$_2$SO3$_4$, filtered and concentrated in vacuo to provide 4k which was directly used in the Pd-catalyzed reaction without further purification.

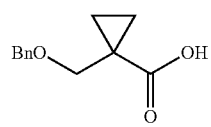 [SMILES: O=C(O)C1(COCc2ccccc2)CC1]

1-((Benzyloxy)methyl)cyclopropane-1-carboxylic acid (4k)
$^1$NMR (600 MHz, CDCl$_3$) δ 7.37-7.32 (m, 4H), 7.31-7.28 (m, 1H), 4.59 (s, 2H), 3.61 (s, 2H), 1.36-1.34 (m, 2H), 0.94-0.93 (m, 2H); $^{13}$C NMR (150 MHz; CDCl$_3$) δ 178.28, 137.83, 128.63, 127.99, 127.91, 73.35, 71.80, 23.55, 14.66.

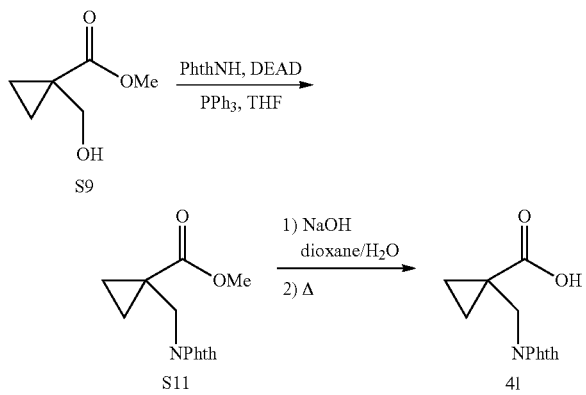

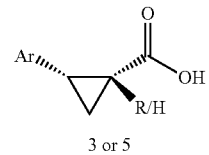

3 or 5

General procedure for enantioselective arylation of cyclopropanecarboxylic acid: A 2-dram vial equipped with a magnetic stir bar was charged with Pd(OAc)2 (4.4 mg, 10 mol %) and L1 (8.8 mg, 20 mol %) in HFIP (0.25 ml). The appropriate cyclopropanecarboxylic acid substrate (0.20 mmol), $Ag_2CO_3$ (82.7 mg, 0.30 mmol), $Na_2CO_3$ (31.8 mg, 0.30 mmol) and aryl iodide (0.40 mmol) was then added. Subsequently, the vial was capped and closed tightly. The reaction mixture was then stirred at the rate of 200 rpm at 80° C. for 16 h. After being allowed to cool to room temperature, the mixture was diluted with ethyl acetate, and 0.1 ml of acetic acid was then added. The mixture was passed through a pad of Celite with ethyl acetate as the eluent to remove any insoluble precipitate. The resulting solution was concentrated, and the residual mixture was dissolved with a minimal amount of acetone and loaded onto a preparative TLC plate. The pure product was then isolated using preparative TLC with ethyl acetate and nexames (¼ to ⅓) as the eluent and 1% v/v of acetic acid as the additive.

Diethyl azodicarboxylate (7.50 mmol) was added to a cooled (0° C.) solution of methyl 1-hydroxymethyl cyclopropanecarboxylate (651 mg, 5.00 mmol), triphenylphosphine (1.97 g, 7.50 mmol) and phthalimide (1.103 g, 7.50 mmol) in THF (12 mL). After being stirred at room temperature for 12 h, the reaction mixture was concentrated undermacuum and purified, by column chromatography on silica gel (eluent: EtOAc/hexanes=1: 5) to give S11.

NaOH (6.00 mmol, 0.240 g) was added to a cooled (0° C.) solution of S11 (3.00 mmol) in dioxane (6 mL) and $H_2O$ (3 mL). The reaction mixture was stirred for 3 h at room temperature, then poured into 2: N HCl (5 mL) and extracted with EtOAc. The combined organic layers were washed with brine, dried over anhydrous $Na_2SO_4$, filtered and concentrated. The residue was heated to 150° C. for 1 h and then cooled to room temperature. The solid was purified by flash chromatography (eluent: EtOAc/hexanes=1:1 with 1% v/v HOAc) to give 4l as white solid.

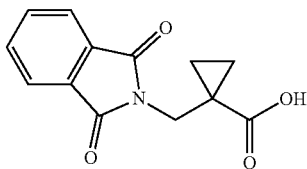 [SMILES: O=C1c2ccccc2C(=O)N1CC1(C(=O)O)CC1]

1-((1,3-Dioxoisoindolin-2-yl)methyl)cyclopropane-1-carboxylic acid (4l)

$^1$H NMR (600 MHz, $CDCl_3$) δ 7.86-7.83 (m, 2H), 7.74-7.70 (m, 2H), 4.01 (s, 2H), 1.38-1.36 (m, 2H), 1.23-1.10 (m, 2H); $^{13}$C NMR (151 MHz, $CDCl_3$) δ 179.98, 168.44, 134.17, 132.04, 123.52, 39.98, 22.48, 15.76.

6[10] and 8[11] were synthesized following the reported procedures.

Enantioselective Arylation of Cyclopropanecarboxylic Acid

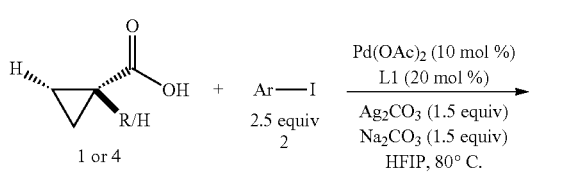

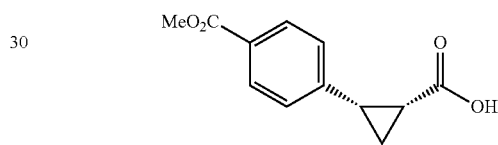

(1R, 2S)-2-(4-(Methoxycarbonyl)phenyl)cyclopropane-1-carboxylic acid (3a)

Substrate 1 was arylated following the general alylation procedure (eluent: hexanes/ethyl acetate=2/1 with 1% v/v of acetic acid). The product was obtained as a white solid (80% yield).

The enantiomeric purity of the substrate was determined by SFC analysis (CHIRALPAK© IA-3 column, 15% (MeOH containing 0.5% $HCO_2H$)/$CO_2$, flow rate 4 mL/min, retention time 1.734 min (major) and 2.616 min (minor), 97:3 er); $^1$H NMR (600 MHz, $CDCl_3$) δ 7.92 (d, J=8.4 Hz, 2H), 7.29 (d, J=8.4 Hz, 2H), 3.91 (s, 3H), 2.63 (q, J=866 Hz, 1H), 2.08 (ddd, J=9.2, 7.9, 5.7 Hz, 1H), 1.69 (dt, J=7.5, 5.4 Hz, 1H), 1.42 (td, J=8.2, 5.2 Hz, 1H); $^{13}$C NMR (150 MHz, $CDCl_3$) δ 176.27, 167.21, 141.51, 129.46, 129.39, 128.74, 52.18, 26.48, 21.81, 12.40;

HRMS (ESI-TOF) m/z Calcd for $C_{12}H_{13}O_4^+$ $[M+H]^+$ 221.0808, found 221.0814;

The absolute stereochemistry was assigned based on comparing the optical rotation of 3s with literature.

3a could also be obtained following standard condition except using cyclopropanecarboxylic acid (0.40 mmol), aryl iodide (0.20 mmol) and $Ag_2CO_3$ (0.20 mmol) as a white solid in the yield of 85% with 96:4 er.

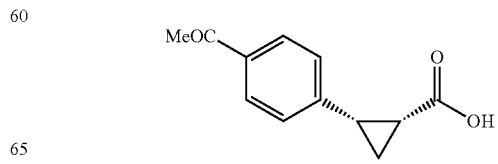

(1R, 2S)-2-(4-acetylphenyl)cyclopropane-1-carboxylic acid (3b)
Substrata 1 was arylated following the general arylation procedure (eluent: hexanes/ethyl acetate=2/1 with 1% v/v of acetic acid). The product was obtained as a white solid (83% yield).
The enantiomeric purity of the substrate was determined by SFC analysis (CHIRALPAK® IG-3 column, 25% (MeOH containing 0.5% $HCO_2H$)/$CO_2$, flow rate 4 mL/min, retention time 1.922 min (minor) and 2.208 min (major), 96:4 er);
$^1$H NMR (600 MHz, $CDCl_3$) δ 7.84 (d, J=8.4 Hz, 2H), 7.32 (d, J=7.8 Hz, 2H), 2.64 (q, J=8.6 Hz, 1H), 2.58 (s, 3H), 2.10 (ddd, J=9.1, 7.9, 5.7 Hz, 1H), 1.71 (dt, J=7,7, 5.4 Hz, 1H), 1.44 (td, J=8.2, 5.2 Hz, 1H); $^{13}$C NMR (150 MHz, $CDCl_3$) δ 198.11, 176.15, 141.79, 135.82, 129.63, 128.20, 26.74, 26.48, 21.86, 12.45;
HRMS (ESI-TOF) m/z Calcd for $C_{12}H_{13}O_3^+$ [M+H]$^+$ 205.0859, found 205.0857;
The absolute stereochemistry was assigned based on comparing the optical rotation of 3s with literature.

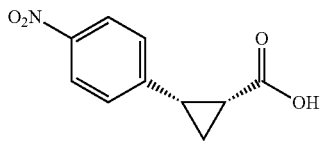 [SMILES: O=C(O)[C@@H]1C[C@@H]1c1ccc([N+](=O)[O-])cc1]

(1R,2S)-2-(4-nitrophenyl)cyclopropane-1carboxylic acid (3c)
Substrate 1 was arylated following the general arylation procedure (eluent: hexanes/ethyl acetate=1/1 with 1% v/v of acetic acid). The product was obtained as a pale-yellow solid (63% yield).
The enantiomeric purity of the substrate was determined by SFC analysis (CHIRALPAK® IG-3 column, 10% (MeOH containing 0.5% $HCO_2H$) $CO_2$, flow rate 4 mL/min, retention time 4.443 min (minor) and 4.907 min (major), 90:10 er);
$^1$H NMR (600 MHz, $CDCl_3$) δ 8.11 (d, J=9.0 Hz, 2H), 7.39 (d, J=8.4 Hz, 2H), 2.67 (q, J=8.5 Hz, 1H), 2.15 (ddd, J=9.0, 8.1, 5.7 Hz, 1H), 1.72 (dt, J=7.6, 5.5 Hz, 1H), 1.50 (td, J=8.2, 5.3 Hz, 1H); $^{13}$C NMR (150 MHz, $CDCl_3$) δ 176.03, 147.00, 143.86, 130.30, 123.29, 26.21, 22.06, 12.73.
HRMS (ESI-TOF) m/z Calcd for $C_{10}H_{10}NO_4^+$ [M+H]$^+$ 208.0604, found 208.0607.
The absolute stereochemistry was assigned based on comparing the optical rotation of 3s with literature.

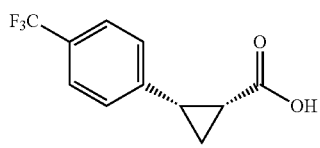 [SMILES: O=C(O)[C@@H]1C[C@@H]1c1ccc(C(F)(F)F)cc1]

(1R,2S)-2-(4-(trifluoromethyl)phanyl)cyclopropane-1-carboxylic acid (3d)
Substrate 1 was arylated following the general arylation procedure (eluent: hexanes/ethyl acetate=4/1 with 1% v/v of acetic acid). The product was obtained as a pale-yellow oil (86% yield).
The enantiomeric purity of the substrate was determined by SFC analysis (CHIRALPAK® AS-3 column, 5% $^i$PrOH/ $CO_2$, flow rate 1.0 mL/min, retention time 5.853 min (major) and 6.402 min (minor), 97:3 er);
$^1$H NMR (600 MHz, $CDCl_3$) δ 7.49 (d, J=8.4 Hz, 2H), 7.32 (d, J=8.4 Hz, 2H), 2.64 (q, J=8.6 Hz, 1H), 2.09 (ddd, J=9.2, 7.8, 5.6 Hz, 1H), 1.69 (dt, J=7 .7, 5.4 Hz, 1H), 1.50 (ddd, J=8.6, 7.8, 5.3 Hz, 1H); NMR (150 MHz, $CDCl_3$) δ 176.59, 140,17, 129.75, 129.12 (q, J=32 Hz), 124.98 (q, J=4 Hz), 124.38 (q, J=270 Hz), 26.25, 21.74, 12.32; $^{19}$F NMR (376 MHz, $CDCl_3$) δ −62.70 (s, 3F);
HRMS (ESI-TOF) m/z Calcd for $C_{11}H_{10}F_3O_2^+$ [M+H]$^+$ 231.0627, found 231.0631.
The absolute stereochemistry was assigned based on comparing the optical rotation of 3s with literature.

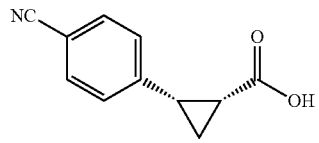 [SMILES: N#Cc1ccc([C@H]2C[C@H]2C(=O)O)cc1]

(1R,2S)-2-(4-cyanophenyl)cyclopropane-1-carboxylic acid (3e)
Substrate 1 was arylated following the general arylation procedure except using AgOAc (3.0 equiv) and $NaHCO_4$ (1.5 equiv) instead of $Ag_2CO_3$ and $Na_2CO_3$. (eluent: hexanes/ethyl acetate=1/1 with 1% v/v of acetic acid). The product was obtained as a pale-yellow solid (53% yield).
The enantiomeric purity of the substrate was determined by SFC analysis (CHIRALPAK® IG-3 column, 15% (MeOH containing 0.5% $HCO_2H$)/$CO_2$, flow rate 4 mL/min, retention time 1.940 min (minor) and 2.366 min (major), 96:4 er);
$^1$H NMR (600 MHz, $CDCl_3$) δ 7.54(d, J=8.4 Hz, 2H), 7.33 (d, J=8.4 Hz, 2H), 2.64 (q, J=8.6 Hz, 1H), 2.12 (ddd, J=9.2, 7.9, 5.7 Hz, 1H), 1.69 (dt, J=7.7, 5.5 Hz, 1H), 1.50 (td, J=8.2, 5.3 Hz, 1H); NMR (150 MHz, $CDCl_3$) δ 176.38, 141.71, 131.84, 130.22, 119.06, 110.68, 26.44, 21.98, 12.43;
HRMS (ESI-TOF) m/z Calcd for $C_{11}H_{10}NO_2^+$ [M+H]$^+$ 188.0706, found 188.0704.
The absolute stereochemistry was assigned based on comparing the optical rotation of 3s with literature.

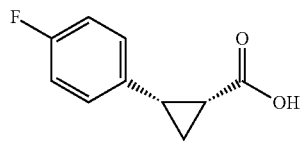 [SMILES: O=C(O)[C@@H]1C[C@@H]1c1ccc(F)cc1]

(1R,2S)-2-(4-fluorophenyl)cyclopropane-1-carboxylic acid (3f)
Substrate 1 was arylated (following the general arylation procedure (eluent: hexanes/ethyl acetate=4/1 with 1% v/v of acetic acid). The product was obtained as a pale-yellow solid (73% yield).
The enantiomeric purity of the substrate was determined by SFC analysis (CHIRALPAK° IG-3 column, 7% ($^i$PrOH containing 0.5% $HCO_2H$)/$CO_2$, flow rate 4 mL/min, retention time 2.492 min (major) and 3.108 min (minor), 96:4 er);
$^1$NMR (600 MHz, $CDCl_3$) δ 7.19 (dd, J=8.4, 5.4 Hz. 2H), 7.32 (d, J=8.7 Hz, 2H), 2.59 (q, J=8.5 Hz, 1H), 2.09 (td, J=8.4, 6.2 Hz, 1H), 1.69 (dt, J=7.8, 5.4 Hz, 1H), 1.50 (ddd, J=8.6, 8.0, 5.1 Hz, 1H); $^1$C NMR (150 MHz, $CDCl_3$) δ 176.27, 161,90 (d, J=243 Hz), 131.71 (d, J=3 Hz), 130.90 (d, J=8 Hz), 114.95 (d, J=21 Hz), 25.87, 21.38, 12.33; $^{19}$F NMR (376 MHz, CDCl$_3$) δ6 -116,17 (s, 1F);

HRMS (ESI-TOF) m/z Calcd for $C_{10}H_{10}FO_2^+$ [M+H]$^+$ 181.0659, found 181.0658.

The absolute stereochemistry was assigned based on comparing the optical rotation of 3s with literature.

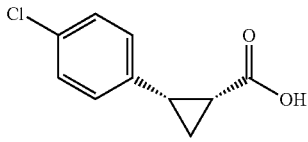 [SMILES: O=C(O)[C@@H]1C[C@@H]1c1ccc(Cl)cc1]

(1R,2S)-2-(4-chlorophenyl)cyclopropane-1-carboxylic acid (3g)

Substrate 1 was arylated following the general arylation procedure (eluent: hexanes/ethyl acetate=4/1 with 1% v/v of acetic acid). The product was obtained as a pale yellow solid (70% yield).

The enantiomeric purity of the substrate was determined by SFC analysis (CHIRALPAK® IA-3 column, 5% (MeOH containing 0.5% HCO$_2$H)/CO$_2$, flow rate 4 mL/min, retention time 3.060 min (major) and 3.580 min (minor), 96:4 er);

$^1$H NMR (600 MHz, CDCl$_3$) δ 7.22 (d, J=8.4, 2H), 7.32 (d, J=8.4 Hz, 2H), 2.58 (q, J=8.6 Hz, 1H), 2.06 (ddd, J=8.2, 7.3, 5.1 Hz, 1H), 1.64 (dt, J=7.7, 5.4 Hz, 1H), 1.39 (ddd, J=8.6, 7.8, 5.1 Hz, 1H); $^{13}$C NMR (150 MHz, CDCl$_3$) δ 175,98, 134.56, 132.72, 130.75,128.26, 25.98, 21.50, 12.31;

HRMS (ESI-TOF) m/z Calcd for $C_{10}H_{10}ClO_2^+$ [M+H]$^+$ 197.0364, found 197.0362.

The absolute stereochemistry was assigned based on comparing the optical rotation of 3s with literature.

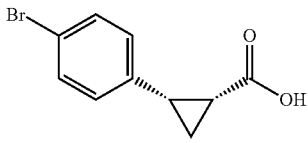 [SMILES: O=C(O)[C@@H]1C[C@@H]1c1ccc(Br)cc1]

(1R,2S)-2-(4-bromophenyl)cyclopropane-1-carboxylic acid (3h)

Substrate 1 was arylated following the general arylation procedure (eluent: hexanes/ethyl acetate=4/1 with 1% v/v of acetic acid). The product was obtained as a pale-yellow solid (81% yield).

The enantiomeric purity of the substrate was determined by SFC analysis (CHIRALPAK® IG-3 column, 15% (MeOH containing 0.5% HCO$_2$H)/CO$_2$, flow rate 4 mL/min, retention time 2.068 min (minor) and 2.275 min (major), 94:6 er);

$^1$H NMR (600 MHz, CDCl$_3$) δ 7.37 (d, J=8.4, 2H), 7.10 (d, J=8.4 Hz, 2H), 2.55 (q, J=8.6 Hz, 1H), 2.04 (ddd, J=9.2, 7.8, 5.6 Hz, 1H), 1.63 (dt, J=7.7, 5.4 Hz, 1H), 1.38 (td, J=8.2, 5.2 Hz, 1H); $^{13}$C NMR (150 MHz, CDCl$_3$) δ 176.92, 135.08, 131.17, 131.13, 120.82, 26,07, 21.63, 12.27;

HRMS (ESI-TOF) m/z Calcd for $C_{10}H_{10}BrO_2^+$ [M+H]$^{30}$ 240.9859, found 240.9856.

The absolute stereochemistry was assigned based on comparing the optical rotation of 3s with literature.

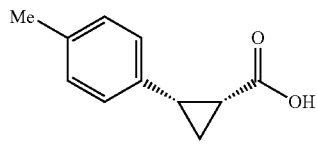 [SMILES: Cc1ccc([C@H]2C[C@H]2C(=O)O)cc1]

(1R,2S)-2-(p-tolyl)cyclopropane-1-carboxylic acid (3)

Substrate 1 was arylated following the general arylation procedure (eluent: hexanes/ethyl acetate=4/1 with 1% v/v of acetic acid). The product was obtained as a pale-yellow solid (73% yield).

The enantiomeric purity of the substrate was determined by SFC analysis (CHIRALPAK® IA-3 column, 7%. (MeOH containing 0.5% HCO$_2$H)/CO$_2$, flow rate 4 mL/min, retention time 1.938 min (major) and 2.725 min (minor), 98:2 er);

$^1$H NMR (600 MHz, CDCl$_3$) δ 7.13 (d, J=7.8, 2H), 7.05 (d, J=7.8 Hz, 2H), 2.59 (q, J=8.6 Hz, 1H), 2.30 (s, 3H), 2.05-2.01 (m, 1H), 1.65-1.62 (m, 1H), 1.35 (td, J=8.1, 5.1 Hz, 1H);

$^{13}$C NMR (150 MHz, CDCl$_3$) δ 175.74, 136.44, 133.01, 129.25, 128.85, 26.33, 21.39, 21.25, 12.23; HRMS (ESI-TOF) m/z Calcd for $C_{11}H_{13}O_2^+$ [M+H]$^+$ 177.0910, found 177.0905.

The absolute stereochemistry was assigned based on comparing the optical rotation of 3s with literature.

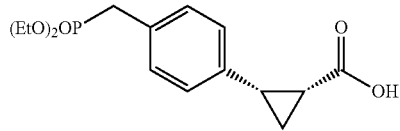

(1R,2S)-2-(4-((diethoxyphosphoryl)methyl)phenyl)cyclopropane-1-carboxylic acid (3j)

Substrate 1 was arylated following the general arylation procedure (eluent: hexanes/ethyl acetate=1/1 with 1% v/v of acetic acid). The product was obtained as a pale-yellow oil (74% yield).

The enantiomeric purity of the substrate was determined by SFC analysis (CHIRALPAK® IG-3 column, 20% (MeOH containing 0.5% HCO$_2$H)/CO$_2$, flow rate 4 mL/min, retention time 1.761 min (minor) and 2.047 min (major), 96:4 er);

$^1$H NMR (600 MHz, CDCl$_3$) δ 7.20 (d, J=7.8, 2H), 7.00 (dd, J=8.1, 2.4 Hz, 2H), 4.03-3.85 (m, 4H), 2.79 (d, J=14.4 Hz, 2H), 2.57 (q, J=9.1 Hz, 1H), 2.10 (ddd, J=9.3, 7.7, 5.7 Hz, 1H), 1.67 (dt, J=7.5, 5.4 Hz, 1H), 1.31 (td, J=8.3, 5.1 Hz, 1H), 1.19 (t, J=7.1 Hz, 3H), 1.16 (t, J=7.1 Hz, 3H); $^{13}$C NMR (150 MHz, CDCl$_3$) δ 174.19, 135.19 (d, J=4 Hz), 129.71 (d, J=10 Hz), 129.61 (d, J=3 Hz), 129.39 (d, J=6 Hz), 62.67 (d, J=7 Hz), 62.54 (d, J=7 Hz), 32.82 (d, J→136 Hz), 25.57, 21.85, 16.39 (d, J=6 Hz), 16.35 (d, J=6 Hz), 11.26; HRMS (ESI-TOF) m/z Calcd for $C_{15}H_{21}O_5P^+$ [M+H]$^+$ 313.1199, found 313.1203.

The absolute stereochemistry was assigned based on comparing the optical rotation of 3s with literature.

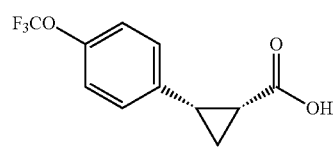 [SMILES: O=C(O)[C@@H]1C[C@@H]1c1ccc(OC(F)(F)F)cc1]

(1R,2S)-2-(4-(trifluoromethoxyl)phenyl)cyclopropane-1-carboxylic acid (3k)
Substrate 1 was arylated following the general arylation procedure (eluent: hexanes/ethyl acetate=4/1 with 1% v/v of acetic acid). The product was obtained as a pale-yellow oil (75% yield).
The enantiomeric purity of the substrate was determined by SFC analysis (CHIRALPAK® IA-3 column, 3% (MeOH containing 0,5% HCO₂H)/CO₂, flow rate 4 mL/min, retention time 2.163 min (major) and 2.503 min (minor), 97:3 er); ¹H NMR (600 MHz, CDCl₃) 7.23 (d, J=8.4, 2H), 7.08 (d, J=7.8 Hz, 2H), 2.59 (q, J=8.6 Hz, 1H); 2.04 (ddd, Jr=9.1, 7.8, 5.6 Hz, 1H), 1.63 (dt, J=7.7, 5.4 Hz, 1H), 1.39 (td, J=8.5, 5.2 Hz. 1H); ¹³C NMR (150 MHz, CDCl₃) δ 177.06, 148.14 (q, J=2 Hz), 134.83, 130.74, 120.63 (q, J=255 Hz), 120.53, 25.88, 21.60, 12.30; ¹⁹F NMR (376 MHz, CDCl₃) δ −8.12 (s, 3F); 11.26;
HRMS (ESI-TOF) m/z Calcd for $C_{11}H_{10}F_3O_3^+$ [M+H]⁺ 247.0577, found 247.0579.
The absolute stereochemistry was assigned based on comparing the optical rotation of 3s with literature.

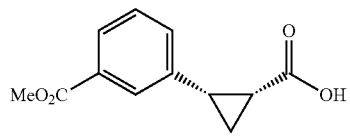 [SMILES: COC(=O)c1cccc([C@H]2C[C@H]2C(=O)O)c1]

(1R,2S)-2-(3-(methoxycarbonyl)phenyl)cyclopropane-1-carboxylic acid (3l)
Substrate 1 was arylated following the general arylation procedure (eluent: hexanes/ethyl acetate=2/1 with 1% v/v of acetic acid). The product was obtained as a white solid (76% yield).
The enantiomeric purity of the substrate was determined by SFC analysis (CHIRALPAK® IG-3 column, 10% (MeOH containing 0.5% HCO₂H)/CO₂, flow rate 4 mL/min, retention time 3.003 min (minor) and 3.428 min (major), 96:4 er); ¹H NMR (600 MHz, COCl₃) δ 7.93 (s, 1H), 7.87 (d, J=7.8 Hz, 1H), 7.40 (d, J=7.2 Hz, 1H), 7.30 (t, J=7.8 Hz, 1H), 3.91 (s, 3H), 2,64 (q, J=8.5 Hz, 1H), 2.08-2.06 (m, 1H), 1.70 (dt, J=7.5, 5.4 Hz, 1H), 1 .41 (td, J=8,2, 5.2 Hz, 1H); ¹³C NMR (150 MHz, CDCl₃) δ 175.99, 167.22, 136.49, 133.86, 130.78, 130.03, 128.25, 128.13, 52.24, 26.27, 21.44, 12.31; HRMS (ESI-TOF) m/z Calcd for $C_{12}H_{13}O_4^+$ [M+H]⁺ 221.9808, found 221.0807.
The absolute stereochemistry was assigned based on comparing the optical rotation of 3s with literature.

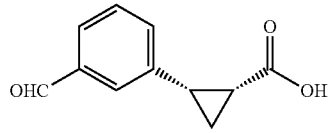 [SMILES: O=Cc1cccc([C@H]2C[C@H]2C(=O)O)c1]

(1R,2S)-2-(3-formylphenl)cyclopropane-1-carboxylic acid (3m)
Substrate 1was arylated following the general arylation procedure except using AgOAc (3.0 equiv) and NaHCO₃ (1.5 equiv) instead of Ag₂CO₃ and Na₂CO₃. (eluent: hexanes/ethyl acetate=2/1 with 1% v/v of acetic acid). The product was obtained as a pale-yellow oil (70% yield).
The enantiomeric purity of the substrate was determined by SFC analysis (CHIRALPAK® IG-3 column, 20% (MeOH containing 0.5% HCO₂H) CO₂, flow rate 4 mL/min, retention time 1.819 min (minor) and 2.479 min (major), 93:7 er): ¹H NMR (600 MHz, d⁶-acetone) δ 10.02 (s, 1H), 7.84 (s, 1H), 7.74 (d, J→7.8 Hz, 1H), 7.62 (d, J=7.8 Hz, 1H), 7.48 (t, J=7.8 Hz, 1H), 2.74 (q, J=8.5 Hz, 1H), 2.21-2.17 (m, 1H), 1.67 (dt, J=7.4, 5.3 Hz, 1H), 1.44 (td, J=8.2, 4.9 Hz, 1H); ¹³C NMR (150 MHz, d⁶-acetone) 193.04, 171.84, 139.29, 137.37, 136.19, 131.16, 129.37, 128.42, 25.53, 22.27, 11.76; HRMS (ESI-TOF) m/2 Calcd for $C_{11}H_{11}O_3^+$[M+H] 191.0703, found 191.0700.
The absolute stereochemistry was assigned based on comparing the optical rotation of 3s with literature.

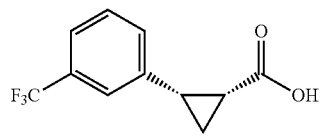 [SMILES: O=C(O)[C@@H]1C[C@@H]1c1cccc(C(F)(F)F)c1]

(1R,2S)-2-(3-(trifluoromethyl)phenyl)cyclopropane-1-carboxylic acid (3n)
Substrate 1 was arylated following the general arylation procedure (eluent: hexanes/ethyl acetate=4/1 with 1% v/v of acetic acid). The product was obtained as a pale-yellow oil (84% yield).
The enanticmeric purity of the substrate was determined by SFC analysis (CHIRALPAK® IG-3 column, 3% (ⁱPrOH containing 0.5% HCO₂H) CO₂, flow rate 4 mL/min, retention time 3.999 min (major) and 4.584 min (minor), 96:4 er); ¹H NMR (600 MHz, CDCl₃) δ 7.48 (s, 1H), 7.45 (d, J=7.8 Hz, 1H), 7.39 (d, J 7.8 Hz, 1H), 7.34 (t, J=7.8 Hz, 1H), 2.64 (q, J=8.5 Hz, 1H), 2.08 (ddd, J=9.1, 7.8, 5.6 Hz, 1H), 1.68 (dt, J=7.7, 5.4 Hz, 1H), 1.43 (ddd, J=8.6, 7.9, 5.2 Hz, 1H); ¹³C NMR (150 MHz, CDCl₃) δ 176.64, 137.05, 132.74, 130.42 (q, J=32 Hz), 128.45, 126.27 (q, J=4 Hz), 124.27 (q, J=270 Hz); 123.76 (q, J=4 Hz), 26.23, 21.60, 12.37; ¹⁹F NMR (376 MHz, CDCl₃) δ −62.89 (s, 3F);
HRMS (ESI-TOF) m/z Calcd for $C_{11}H_{10}F_3O_2^+$ [M+H]⁺ 231.0027, found 231.0628.
The absolute stereochemistry was assigned based on comparing the optical rotation of 3s with literature.

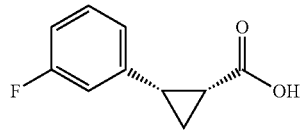

(1R,2S)-2-(3-fluorophenyl)cyclopropane-1-carboxylic acid (3o)
Substrate 1 was arylated following the general arylation procedure (eluent: hexanes/ethyl acetate=4/1 with 1% v/v of acetic acid). The product was obtained as a pale-yellow oil (79% yield).
The enantiomeric purity of the substrate was determined by SFC analysis (CHIRALPAK® IA-3 column, 2% (MeOH containing 0.5% HCO₂H) CO₂, flow rate 4 mL/min, retention time 4.482 min (major) and 5.337 min (minor), 97:3 .er);
¹H NMR (600 MHz, CDCl₃) δ 7.20 (td, J'=7.9, 6.1 Hz, 1H), 7.01 (dt, J=7.8, 0.8 Hz, 1H), 6.93 (d, J=10.2 Hz, 1H), 6.89 (td, J=8.4, 2.5 Hz, 1H), 2.60 (q, J=8.6 Hz, 1H), 2.05 (ddd, J=9.2, 7.8, 5.6 Hz, 1H), 1.64 (dt, J=7.7, 5.4 Hz, 2H), 1.38 (ddd, J=8.6, 7.8, 5.1 Hz, 1H); ¹³C NMR (150 MHz, CDCl₃)

δ 176.56, 162.64 (d, J=245 Hz), 138.66 (d, J=8 Hz), 129.47 (d, J=9 Hz), 125.14 (d, J=2 Hz), 116.30 (d, J=21 Hz), 113.92 (d, J=21 HZ), 26.22, 21.57, 12.31; $^{19}$F NMR (376 MHz, CDCl$_3$) δ −114.29 (s, 1F);
HRMS (ESI-TOF) m/z Calcd for $C_{10}H_{10}FO_2{}^+$ [M+H]$^+$ 181.0659, found 181.0658.
The absolute stereochemistry was assigned based on comparing the optical rotation of 3s with literature.

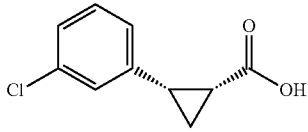 [SMILES: O=C(O)[C@@H]1C[C@@H]1c1cccc(Cl)c1]

(1R,2S)-2-(3-chlorophenyl)cyclopropane-1-carboxylic acid (3p)
Substrate 1 was arylated following the general arylation procedure (eluent: hexanes/ethyl acetate=4/1 with 1% v/v of acetic acid). The product was obtained as a pale-yellow oil (80% yield).
The enantiomeric purity of the substrate was determined by SFC analysis (CHIRALPAK® IA-3 column, 3% (MeOH containing 0.5% HCO$_2$H)/CO$_2$, flow rate 4 mL/min, retention time 4.252 min (major) and 5.031 min (minor), 96:4 er);
$^1$H NMR (600 MHz, CDCl$_3$) δ 7.24 (s, 1H), 7.19-7.15 (m, 2H), 7.11-7.09 (m, 1H), 2.58 (q, J=8.6 Hz, 1H), 2.05 (ddd, J=9.2, 7.8, 5.6 Hz, 1H), 1.84 (dt, J=7.7, 5.4 Hz, 1H), 1.38 (ddd, J=8.6, 7.8, 5.2 Hz, 1H); $^{13}$C NMR (150 MHz, CDCl$_3$) δ 176.48, 138.14, 133.88, 129.65, 129.29, 127.58, 127.19, 26.17, 21.51, 12.29;
HRMS (ESI-TOF) m/z Calcd for $C_{10}H_{10}ClO_2{}^+$ [M+H]$^+$ 197.0364, found 197.0361.
The absolute stereochemistry was assigned based on comparing the optical rotation of 3s with literature.

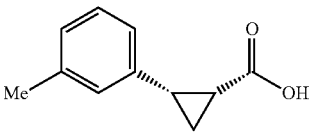

(1R,2S)-2-(m-tolyl)cyclopropane-1-carboxylic acid (3q)
Substrate 1 was arylated following the general arylation procedure (eluent: hexanes/ethyl acetate=4/1 with 1% v/v of acetic acid). The product was obtained as a pale-yellow oil (71% yield).
The enantiomeric purity of the substrate was determined by SFC analysis (CHIRALPAK® IA-3 column, 5% MeOH/CO$_2$, flow rate 4 mL/min, retention time 2.136 mm (major) and 2.547 min (minor), 97:3 er);
$^1$H NMR (600 MHz, CDCl$_3$) δ 7,13 (t, J=7.8 Hz, 1H), 7.06 (s, 1H), 7.03 (d, J=7.8 Hz, 1H), 7.01 (d, J=7.8 Hz, 1H), 2.59 (q, J=8.6 Hz, 1H), 2.33 (s, 3H), 2.01 (ddd; J=9.2, 7.8; 5.6 Hz, 1H), δ 1.65 (dt, J=7.7. 5.3 Hz, 1H), 1.35 (td, J=8.2, 5.0 Hz, 1H); $^{13}$C NMR (150 MHz, CDCl$_3$) δ 176.10, 137.61, 135.95, 130.22, 127.97, 127.73, 126.35, 26.62, 21.49, 21.35, 12.18;
HRMS (ESI-TOF) m/z Calcd for $C_{11}H_{13}O_{2+}$ [M+H]$^+$ 177.0910, found 177.0905.
The absolute stereochemistry was assigned based on comparing the optical rotation of 3s with literature.

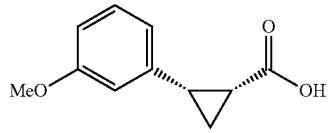 [SMILES: COc1cccc([C@H]2C[C@H]2C(=O)O)c1]

(1R,2S)-2-(3-methoxyphenyl)cyclopropane-1-carboxylic acid (3r)
Substrate 1 was arylated following the general arylation procedure (eluent: hexanes/ethyl acetate=4/1 with 1% v/v of acetic acid). The product was obtained as a pale-yellow oil (70% yield).
The enantiomeric purity of the substrate was determined by SFC analysis (CHIRALPAK® IA-3 column, 10% (MeOH containing 0.5% HCO$_2$H)/CO$_2$, flow rate 4 mL/min retention time 1.670 min (major) and 2.114 min (minor), 97:3 er);
$^1$H NMR (600 MHz, CDCl$_3$) δ 7.15 (t, J=7.8 Hz, 1H), 6.82 (d, J=7.8 Hz, 1H), 6.78 (s,1H), 6.74 (cd, J=8.4, 3.2 Hz, 1H), 3.76 (s, 3H), 2.59 (q, J=8.7 Hz, 1H), 2.02 (ddd, J=9.3, 7.7, 5.6 Hz, 1H), 1.63 (dt, J=7,7, 5.3 Hz, 1H), 1.35 (td, J=8.2, 5.0 Hz, 1H); $^{13}$C NMR (150 MHz, CDCl$_3$) δ 177.04, 159.37, 137.72, 129.05, 121.83, 114.90, 112.66, 55.26, 26.71, 21.56, 12.35;
HRMS (ESI-TOF) m/z Calcd for $C_{11}H_{13}O_3{}^+$ [M+H]$^+$ 193.0859, found 193.0861.
The absolute stereochemistry was assigned based on comparing the optical rotation of 3s with literature:

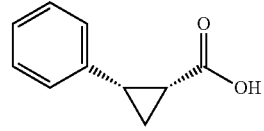 [SMILES: O=C(O)[C@@H]1C[C@@H]1c1ccccc1]

(1R,2S)-2-phenylcyclopropan-1-carboxylic acid (3s)
Substrate 1 was arylated following the general arylation procedure (eluent: hexanes/ethyl acetate=4/1 with 1% v/v of acetic acid). The product was obtained as a pale-yellow oil (70% yield).
The enantiomeric purity of the substrate was determined by SFC analysis (CHlRALPAK® IA-3 column, 10% (MeOH containing 0.5% HCO$_2$H)/CO$_2$, flow rate 4 mL/min, retention time 1,492 min (major) and 1.730 min (minor), 95:5 er);
$^1$H NMR (600 MHz, CDCl$_3$) δ 7.25-7.22 (m, 3H), 7.21-7.18 (m, 1H), 2.62 (q, J=8.7 Hz, 1H), 2.04 (ddd, J=9.0, 7.9, 5.7 Hz, 1H), 1.66 (dt, J=7.7, 5.3 Hz, 1H), 1.37 (td, J=8.2, 5.1 Hz, 1H); $^{13}$C NMR (150 MHz, CDCl$_2$) δ 176.20, 136.07, 129.40, 128.10, 126.92, 26.64, 21.42, 12.16;
HRMS (ESI-TOF) m/z Calcd for $C_{10}H_{11}O_2{}^+$ [m+H]$^+$ 163.0754, found 163.0752.
The absolute stereochemistry was assigned based on known optical rotation. $^{12}[α]^{23}{}_D$=,−23.1° (c=1, CHCl$_3$), lit $[α]^{12}{}_D$=−27.6° (c=1.00, CHCl$_3$)

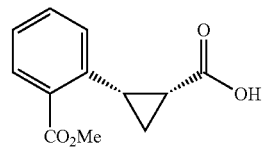 [SMILES: COC(=O)c1ccccc1[C@H]1C[C@H]1C(=O)O]

(1R, 2S)-2-(2-(methoxycarbonyl)phenyl)cyclopropane-1-carboxylic acid (3t)
Substrate 1 was arylated following the general arylation procedure (eluent: hexanes/ethyl acetate=2/1 with 1% v/v of acetic acid). The product was obtained as a white solid (84% yield).
The enantiomeric purity of the substrate was determined by SFC analysis (CHIRALPAK® IG-3 column, 15% (MeOH containing 0.5% HCO2H)/CO$_2$, flow rate 4 mL/min, retention time 1.947 min (minor) and 2.349 min (major), 98:2 er);
$^1$H NMR (600 MHz, CDCl3) δ 7.84 (d, J=7.8 Hz, 1H), 7.42 (td, J=8.0, 1.2 Hz, 1H), 7.32 (d, J=7.8 Hz, 1H), 7.28 (t, J=8.0 Hz, 1H), 3.82 (s, 1H), 2.98 (q, J=8.6 Hz, 1H), 2.12 (ddd, J=9.2, 8.0, 5.6 Hz, 1H), 1.61 (dt, J=8.0, 5.3 Hz, 1H), 1.44 (td, J=8:1, 5.0 Hz, 1H); $^{13}$C NMR (150 MHz, CDCl$_3$) δ 177.16, 167.92, 137.77, 131.75, 131.25, 131.04, 130.26, 126.94, 52.12, 26.48, 21.87, 13.60;
HRMS (ESI-TOF) m/z Calcd for $C_{12}H_{12}O_3^+$ [M+H]$^+$ 221.0808, found 221.0807.
The absolute stereochemistry were assigned based on comparing the optical rotation of 3s with literature.

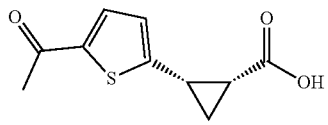

(1R,2S)-2-(5-acetylthiophen-2-yl)cyclopropane-1-carboxylic acid (3u)
Substrate 1 was arylated following the general acylation procedure (eluent: hexanes/ethyl acetate=1/1 with 1% v/v of acetic acid). The product was obtained as a pale-yellow solid (65% yield).
The enantiomeric purity of the substrate was determined by SFC analysis. (CHIRALPAK® IG-3 column, 25% (MeOH containing 0.5% HCO$_2$H)/CO$_2$, flow rate 4 mL/min, retention time 1.996 min (minor) and 2.557 min (major), 95:5 er);
$^1$H NMR (600 MHz, CDCl$_3$) δ 7.51 (d, J=3,6 Hz, 1H), 6.89 (dd, J=3.9, 0.9 Hz, 1H), 2.66 (q, J=8.1 Hz, 1H), 2.64 (s, 3H), 2.15 (ddd, J=8.9, 7.9, 6.0 Hz, 1H), 1.70 (dt, J=7.4, 5.8 Hz, 1H), 1.53 (ddd, J=8.2, 8.0, 5.2 Hz); $^{13}$C NMR (150 MHz, CDCl$_3$) δ 190.70, 175.32, 149.33, 143.15, 132.64, 127.86, 26.67, 22.76, 21.24, 14.27;
HRMS (ESI-TOF) m/z Calcd for $C_{10}H_{11}O_3S^+$ [M+H]$^+$ 211.0423, found 211.0428.
The absolute stereochemistry was assigned based on comparing the optical rotation of 3s with literature.

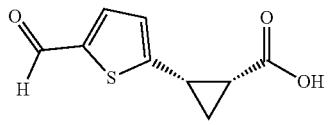 [SMILES: O=Cc1ccc([C@H]2C[C@H]2C(=O)O)s1]

(1R,2S)-2-(5-formylfuran-2-yl)cyclopropane-1-carboxylic acid (3v)
Substrate 1 was arylated following the general arylation procedure (eluent: hexanes/ethyl acetate=1/1 with 1% v/v of acetic acid). The product was obtained as a pale-yellow solid (67% yield).
The enantiomeric purity of the substrate was determined by SFC analysis (CHIRALPAK® AS-3 column, 10% $^i$PrOH/CO$_2$, flow rate 1.0 mL/min, retention time 9.843 min (major) and 11.226 min (minor), 96:4 er);

$^1$H NMR (600 MHz, CDCl$_3$) δ 9.51 (s, 1H), 7.16 (d, J=3.6 Hz, 1H), 6.35 (dd, J=3.6, 0.5 Hz, 1H), 2.58 (q, J=8.5 Hz, 1H), 2.16 (ddd, J=8,5, 8.0, 6.2 Hz, 1H), 1.71 (ddd, J=7.2, 6.0, 5.4 Hz, 1H), 1.54 (ddd, J=8.2. 8.1, 5.1 Hz, 1H); $^{13}$C NMR (150 MHz, CDCl$_3$) (1C overlapped) δ 177.17, 175.16, 157.97, 152.09, 111.05, 21.48, 18.88, 12.63:
HRMS (ESI-TOF) m/z Calcd for $C_9H_9O_4^+$ [M+H]$^+$ 181.0495, found 181.0495.
The absolute stereochemistry was assigned based on comparing the optical rotation of 3s with literature.

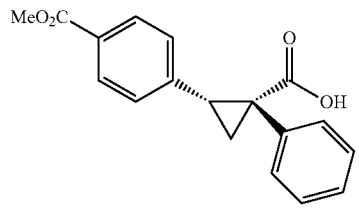 [SMILES: COC(=O)c1ccc([C@H]2C[C@]2(C(=O)O)c2ccccc2)cc1]

(1R,2R)-2-(4-(methoxycarbonyl)phenyl)-1-phenylcyclopropane-1-carboxylic acid (5a)
Substrate 4a was arylated following the general arylation procedure (eluent: hexanes/ethyl acetate=2/1 with 1% v/v of acetic acid). The product was obtained as a white solid (76% yield).
The enantiomeric purity of the substrate was determined by SFC analysis (CHIRALPAK®
AD-3 column, 20% $^i$PrOH/CO$_2$, flow rate 2.0 mL/min, retention time 6.718 min (major) and 8.227 min (minor), 98:2 er);
$^1$H NMR (600 MHz, CDCl$_3$) δ 7.96 (d, J=7.8 Hz, 2H), 7.44 (d, J=7.2 Hz, 2H), 7.38-7.34 (m, 4H), 7.30 (tt, J=7.2, 1.5 Hz, 1H), 3.93 (s, 3H), 2.90 (t, J=8.4 Hz, 1H), 2.28 (dd, J=7.8, 4.8 Hz, 1H), 1.70 (dd, J=9.0, 4.8 Hz, 1H); $^{13}$C NMR (150 MHz, CDCl$_3$) δ 176.30, 167.21, 141.47, 139.46, 130.36, 129.53, 129.36, 128,82, 128.64, 127.82, 52.22, 38.01, 34.56, 19.39;
HRMS (ESI-TOF) m/z Calcd for $C_{18}H_{18}O_4Na^+$ [M+Na]$^+$ 319.0941, found 319.0943.
The absolute stereochemistry was assigned based on comparing the optical rotation of 3s with literature.

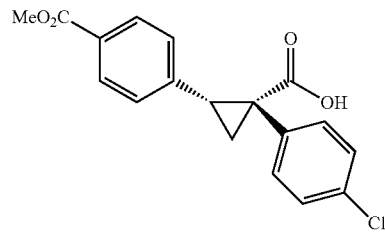 [SMILES: COC(=O)c1ccc([C@H]2C[C@]2(C(=O)O)c2ccc(Cl)cc2)cc1]

(1R,2R)-1-(4-chlorophenyl)-2-(4-(methoxycarbonyl)phenyl)cyclopropane-1-carboxylic acid (5b)
Substrate 4b was acrylated following the general arylation procedure (eluent: hexanes/ethyl acetate=2/1 with 1% v/v of acetic acid). The product was obtained as a white solid (80% yield).
The enantiomeric purity of the substrate was determined by SFC analysis (CHIRALPAK® AD-3column, 20% $^i$PrOH/CO$_2$, flow rate 2.0 mL/min, retention time 6.030 min (major) and 9.105 min (minor), 99:1 er);
$^1$H NMR (600 MHz, CDCl$_3$) δ 7.96 (d, J=8.4 Hz, 2H), 7.37 (dt, J=8.4, 2.1 Hz, 2H), 7.34 (d, J=8.4 Hz, 2H), 7.32 (dt, J=9.0, 2.2 Hz, 2H), 3.94 (s, 3H), 2.85 (t, J=8.4 Hz, 1H), 2.27 (dd, J=7.8, 5.1 Hz, 1H), 1.68 (dd, J=9.0, 5.1, 1H); $^{13}$C NMR (150 MHz, CDCl$_3$) δ 175.90, 167.17, 141.05, 137.89, 183.75, 131.74, 129.56, 129.34, 128.96, 128.73, 52.27, 37.28, 34.78, 19.41;
HRMS (ESI-TOF) m/z Calcd. for $C_{15}H_{16}ClO_4^+$ [M+H]$^+$ 331.0732, found 331.0724.
The absolute stereochemistry was assigned based on comparing the optical rotation of 3s with literature.

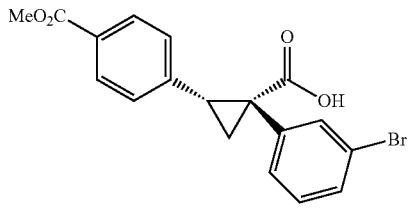 [SMILES: COC(=O)c1ccc([C@H]2C[C@]2(C(=O)O)c2cccc(Br)c2)cc1]

(1R,2R)-1-(3-bromophenyl)-2-(4-(methoxycarbonyl)phenyl)cyclopropane-1-carboxylic Acid (5c)
Substrate 4c was arylated following the general arylatibn procedure (eluent: hexanes/ethyl acetate=2/1 with 1% v/v of acetic acid). The product was obtained as a colorless oil (90% yield).
The enantiomeric purity of the substrate was determined by SFC analysis (CHIRALPAK®
AD-3 column, 20% $^i$PrOH/CO$_2$, flow rate 2.0 mL/min, retention time 6.137 min (major) and 6.920 min (minor), 98:2 er);
$^1$H NMR (600 MHz, CDCl$_3$) δ 7.96 (d, J=8.4 Hz, 2H), 7.58.(t, J=1.8 Hz, 1H), 7.43 (ddd, J=8.1, 1.8, 0.9 Hz, 1H), 7.38 (d, J=7.8 Hz, 1H), 7.35 (d, J=7.8 Hz, 2H), 7.22 (t, J=7.8 Hz, 1H), 3.95 (s, 3H), 2,88 (t, J=8.4 Hz, 1H), 2.27 (dd, J=7,8, 5.2 Hz, 1H), 1.70 (dd, J=9.1, 5.1 Hz, 1H); NMR (150 MHz, CDCl$_3$) δ 175.75, 167.16, 141.55, 140.89, 133.39, 131.02, 130.07, 129.58, 129.35, 129.17, 129.01, 122,37, 52.28, 37.47, 34.65, 19.43.
HRMS (ESI-TOP) m/s Calcd for $C_{18}H_{18}BrO_4^+$ [M+H]$^+$ 375.0226, found 375.0237.
The absolute stereochemistry was assigned based on comparing the optical rotation of 3s with literature.

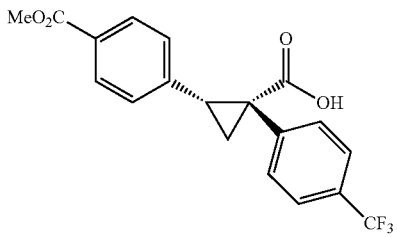 [SMILES: COC(=O)c1ccc([C@H]2C[C@]2(C(=O)O)c2ccc(C(F)(F)F)cc2)cc1]

(1R,2R)-2-(methoxycarbonyl)phenyl)-1-(4-(trifluoromethyl)phenyl)cyclopropane-1-carboxylic acid,(5d)
Substrate 4d was arylated following the general arylation procedure (eluent: hexanes/ethyl acetate=2/1 with 1% v/v of acetic acid). The product was obtained as a white oil (85% yield).
The enantiomeric purity of the substrate was determined by SFC analysis (CHIRALPAK® AD-3 column, 20% $^i$PrOH/CO$_2$, flow rate 2.0 mL/min, retention time 2.852 min (major) and 3.471 min (minor), 99:1 er);
$^1$H NMR (600 MHz, CDCl$_3$) δ 7.98 (d, J=7.8 Hz, 2H), 7.62 (d, J=8:4 Hz, 2H), 7.57 (d, J=8.4 Hz, 2H), 7.38 (d, J=7.8 Hz, 2H), 3.94 (s, 3H), 2.91 (t, J=8.4 Hz, 1H), 2.34 (dd, J=7.5, 5.2 Hz, 1H), 1,74 (d, J=9.0, 5.4 Hz, 1H); $^{13}$C NMR (150 MHz, CDCl$_3$) δ 175.04, 167.13, 143.21, 140.78, 130.80, 130.10 (q, J=33 Hz), 129.78, 129.36, 129.13, 125.56 (q, J=4.0 Hz), 124.13 (q, J=272 Hz) 52.30, 37,54, 34.63, 19.38; $^{19}$F NMR (376 MHz, CDCl$_3$) δ −62.84 (s, 3F);
HRMS (ESI-TOF) m/z Calcd for $C_{19}H_{18}F_2O_4^+$ [M+H]$^+$ 365.0995, found 365.0994.
The absolute stereochemistry was assigned based on comparing the optical rotation of 3s with literature.

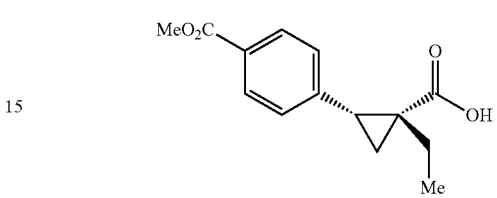

(1R,2R)-1-ethyl-2-(4-(methoxycarbonyl)phenyl)cyclopropane-1-carboxylic acid (5e)
Substrate 4e was arylated following the general arylation procedure except at 60° C. (eluent: hexanes/ethyl acetate=2/1 with 1% v/v of acetic acid). The product was obtained as a pale-yellow solid (71% yield).
The enantiomeric purity of the substrate was determined by SFC analysis (CHIRALPAK® IA-3 column, 20% (MeOH containing 0.5% HCO$_2$H) CO$_2$, flow rate 4 mL/min, retention time 1.595 min (major) and 1.873 min (minor), 95:5 er);
$^1$H NMR (600 MHz, CDCl$_3$) δ 7.90 (d, J=8.4 Hz, 2H), 7.23 (d, J=8.4 Hz, 2H), 3.90 (s, 3H), 2.40 (t, J=8.1 Hz, 1H), 2.04-1.98 (m, 1H), 1.88 (dd, J=7.2, 5.4 Hz, 1H), 1,46-1.40 (m, 1H), 1.18 (dd. J=8.4, 4.8 Hz, 1H), 1.05 (t, J=7.2 Hz, 3H); $^{13}$C NMR (150 MHz, CDCl3) δ 177.71, 167.26, 142.28, 129.32, 129.22, 128.42, 52.13, 34.30, 33.52, 28.64, 18.69, 11.93;
HRMS (ESI-TOF) m/z Calcd for $C_{14}H_{17}O_4^+$ [M+H]$^δ$ 249.1121, found 249.1124.
The absolute stereochemistry was assigned based on comparing the optical rotation of 3s with literature.

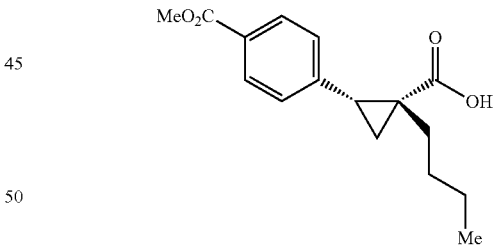

(1R,2R)-1-butyl-2-(4-(methoxycarbonyl)phenyl)cyclopropane-1-carboxylic acid (5f)
Substrate 4f was arylated following the general arylation procedure except at 60° C. (eluent: hexanes/ethyl acetate=2/1 with 1% v/v of acetic acid). The product was obtained as a pale-yellow solid (76% yield).
The enantiomeric purity of the substrate was determined by SFC analysis (CHIRALPAK® AD-3 column; 20% $^i$PrOH/CO$_2$, flow rate 2.0 mL/min, retention time 3.332 min (major) and 3.850 min (minor), 95:5 er);
$^1$H NMR (600 MHz, CDCl3) δ 7.90 (d, J=8.4 Hz, 2H), 7.23 (d, J=8.4 Hz, 2H), 3.90 (s, 3H), 2.39 (t, J=8.1 Hz, 1H), 2.07-2.02 (m, 1H), 1.89 (dd, J=7.2, 5.4 Hz, 1H), 1.52-1.40 (m, 2H), 1.36-1.30 (m, 3H), 1.19 (dd, J=8.6, 5.1 Hz, 1H), 0.91 (t, J=7.2 Hz, 3H); $^{13}$C NMR (150 MHz, CDCl$_3$) δ 177.47, 167.25, 142.27, 129.33, 129.20, 128.44, 52.14, 35.47, 33.60, 33.39, 29.93, 22.90, 18.79, 14.12;
HRMS (ESI-TOF) m/z Calcd for $C_{18}H_{20}O_4^+$ [M+H]$^+$ 277.1434, found 277.1437.
The absolute stereochemistry was assigned based on comparing the optical rotation of 3s with literature.

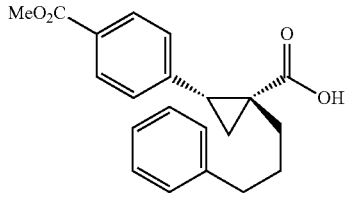 [SMILES: COC(=O)c1ccc([C@H]2C[C@@]2(CCCc2ccccc2)C(=O)O)cc1]

(1R,2R)-2-(4-(methoxycarbonyl)phenyl)-1-(3-phenylpropyl)cyclopropane-1-carboxylic acid (5g)
Substrate 4g was arylated following the general arylation procedure except at 60° C. (eluent: hexanes/ethyl acetate=2/1 with 1% v/v of acetic acid). The product was obtained as a pale-yellow oil (58% yield).
The enantiomeric purity of the substrate was determined by SFC analysis (CHIRALPAK® AD-3 column, 20% $^i$PrOH/CO$_2$, flow rate 2.0 mL/min, retention the 7.925 min (major) and 9.066 min (minor), 96:4 er);
$^1$H NMR (600 MHz, CDCl3) δ 7.89 (d, J=9.4 Hz, 2H), 7.28 (t, J=8.1 Hz, 2H), 7.22-7.17 (m, 5H), 3.89 (s, .3H), 2.63 (t, J=7.8 Hz, 2H) 2.36 (d, J=7.5 Hz, 1H), 2.08-2.02 (m, 1H), 1.90-1.80 (m, 3H), 1.41-1.36 (m, 1H), 1.67 (dd, J=8.4, 4.8 Hz, 1H); $^{13}$C NMR (150 MHz, CDCl$_3$) δ 177.46, 167.23, 142.14, 142.07, 129.33, 129.22, 129.19, 128.49, 128.47, 125.95, 52.14, 35.95, 35.33, 33.70, 33.14, 29.35, 18.95;
HRMS (ESI-TOF) m/z Calcd for $C_{21}H_{23}O_4^+$ [M+H]$^+$ 339.1591, found 339.1595,
The absolute stereochemistry was assigned based on comparing the optical rotation of 3s with literature.

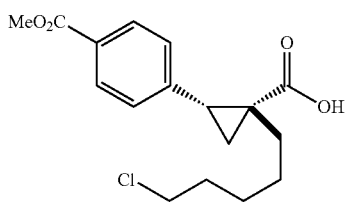 [SMILES: COC(=O)c1ccc([C@H]2C[C@@]2(CCCCCCl)C(=O)O)cc1]

(1R,2R)-1-(5-chloropentyl)-2-(4-(methoxycarbonyl)phenyl)cyclopropane-1-carboxylic acid (5h)
Substrate 4h was arylated following the general arylation procedure except at 60° C. (eluent: hexanes/ethyl acetate=2/1 with 1% v/v of acetic acid). The product was obtained as a pale-yellow oil (80% yield).
The enantiomeric purity of the substrate was determined by SFC analysis (CHIRALPAK® AD-3 column, 20% $^i$PrOH/CO$_2$, flow rate 2.0 mL/min, retention time 4.610 min (major) and 5.459 min (minor), 96:4 er);
$^1$H NMR (600 MHz, CDCl$_3$) δ 7.90 (d, J=8.4 Hz, 2H), 7.23 (d, J=7.8 Hz, 2H), 3.91 is, 3H), 3.54 (t, J=6.6 Hz, 2H), 2.40 (t, J=8.1 Hz, 1H), 2.08-2.04 (m, 1H), 1.91 (dd, J=7.2, 5.4 Hz, 1H), 1.79 (p, J=6.7 Hz, 2H), 1.59-1.43 (m, 4H), 1.38-1.32 (m, 1H), 1.21 (dd, J=8.7, 5.0 Hz, 1H); $^{13}$C NMR (150 MHz, CDCl$_3$) δ 177.17, 167.23, 142.05, 129.36, 129.23, 128.54, 52.18, 45.15, 35.59, 33.69, 33.17, 32.54, 27.07, 27.02, 18.89;

HRMS (ESI-TOF) m/z Calcd for $C_{17}H_{22}ClO_4^+$ [M+H]$^+$ 325.1201, found 325.1205.
The absolute stereochemistry was assigned based on comparing the optical rotation of 3s with literature.

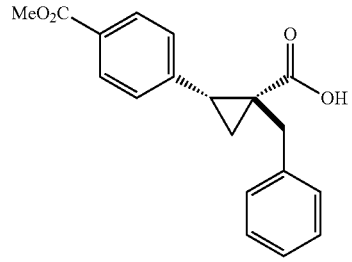 [SMILES: COC(=O)c1ccc([C@H]2C[C@@]2(Cc2ccccc2)C(=O)O)cc1]

(1S,2R)-1-benzyl-2-(4-(methoxycarbonyl)phenyl)cyclopropane-1-carboxylic acid (5i)
Substrate 4i was arylated following the general arylation procedure except using AgOAc (3.0 equiv) and NaHCO$_3$ (1.5 equiv) instead of Ag$_2$CO$_3$ and Na$_2$CO$_3$ at 60° C. (eluent: hexanes/ethyl acetate=2/1 with 1% v/v of acetic acid). The product was obtained as a pale-yellow solid (63% yield).
The enantiomeric purity of the substrate was determined by SFC analysis (CHIRALPAK® AS-3 column, 20% $^i$PrOH/CO$_2$, flow rate 2.0 mL/min, retention time 2.409 min (major) and 2.993 min (minor), 96:4 er);
$^1$H NMR (600 MHz, CDCl$_3$) δ 7.89 (d, J=8.4 Hz, 2H), 7.31-7.28 (m, 2H), 7.24-7.20 (m, 5H), 3.91 (s, 3H), 3.49 (d, J=15.0 Hz, 1H), 2.82 (d, J=15.0 Hz, 1H), 2.47 (t, J=8.1 Hz, 1H), 1.98 (dd, J=7.2, 5.4 Hz, 1H), 1.33 (dd, J=8.7, 5.3 Hz, 1H); $^{13}$C NMR (150 MHz, CDCl$_3$) δ 176.91, 167.22, 141.86, 138.65, 129.38, 129.34, 129.21, 128.53, 126.73, 52.17, 39.71, 33.48, 32.89, 18.00;
HRMS (ESI-TOF) m/z Calcd for $C_{19}H_{19}O_4^+$ [M+H]$^+$ 311.1278, found 311.1283.
The absolute stereochemistry was assigned based on comparing the optical rotation of 3s with literature.

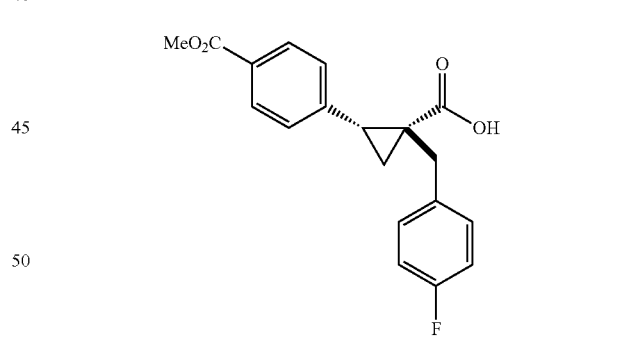

(1S,2R)-1 -(4-fluorobenzyl)-2-(4-(methoxycarbonyl)phenyl)cyclopropane-1-carboxylic acid (5j)
Substrate 4j was arylated following the general arylation procedure except using AgOAc (3.0 equiv) and NaHCO$_3$ (1.5 equiv) instead of Ag$_2$CO$_3$ and Na$_2$CO$_3$ at 60° C. (eluent: hexanes/ethyl acetate=2/1 with 1% v/v of acetic acid). The product was obtained as a pale-yellow solid (64% yield).
The enantiomeric purity of the substrate was determined by SFC analysis (CHIRALPAK® As-3 column, 20% $^i$PrOH/CO$_2$, flow rate 2.0 mL/min, retention time 2.211 min (major) and 2.593 min (minor), 96:4 er);
$^1$H NMR (600 MHz, CDCl3) δ 7.89 (d, J=8.4 Hz, 2H), 7.21-7.18 (m, 4H), 6.97 (t, J=8.7 Hz, 2H), 3.91 (s, 3H), 3.45

(d, J=14.4 Hz, 1H), 2.74 (d, J=14.4 Hz, 1H), 2.47 (t, J=8.2 Hz, 1H) 1.98 (t, J=6.3 Hz, 1H), 1.33 (dd, J=8.7, 5.3 Hz, 1H); $^{13}$C NMR (150 MHz, CDCl$_3$) δ 176.95, 167.19, 161:85 (d, J=243 Hz), 141.67, 134.43 (d, J=3 Hz), 130.69 (d, J=10 Hz), 129.38, 129.17; 128.65, 115.33 (d, J=21 Hz), 52.19, 39.10, 33.67, 32.98, 18.11; $^{19}$F NMR (376 MHz, CDCl$_3$) δ 116.67 (s, 1F);
HRMS (ESI-TOF) m/z Calcd for $C_{19}H_{18}FO_4^+$ [M+H] 329.1184, found 329.1185.
The absolute stereochemistry was assigned based on comparing the optical rotation of 3s with literature.

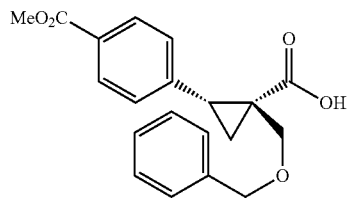 [SMILES: COC(=O)c1ccc([C@H]2C[C@@]2(COCc2ccccc2)C(=O)O)cc1]

(1R,2R)-1-((benzyloxy)methyl)-2-(4-(methoxycarbonyl) phenyl)cyclopropane-1-carboxylic acid (5k)
Substrate 4k was arylated following the general arylation (eluent: hexanes/ethyl acetate 2/1 with 1% v/v of acetic acid). The product was obtained as a pale-yellow solid (65% yield).
The enantiomeric purity of the substrate was determined by SFC analysis (CHIRALPAK® AS-3 column, 20% $^i$PrOH CO$_2$, flow rate 2.0 mL/min, retention time 2.840 min (major) and 3.398 min (minor), 96:4 er);
$^1$H NMR (600 MHz, CDCl$_3$) δ 7.91 (d, J=7.8 Hz, 2H), 7.37-7.33 (m, 4H), 7.32-7.29 (m, 1H), 7.26 (d, J=8.4 Hz, 2H), 4.60 (s, 2H), 3.89 (s, 3H), 3.86 (d, J=10.2 Hz, 1H), 3.63 (d, J=10.2 Hz, 1H), 2.59 (t, J=8.4 Hz, 1H), 1.99 (dd, J=7.7, 5.3 Hz, 1H), 1.42 (dd, J=8.9, 5.2 Hz, 1H); $^{13}$C NMR (150 MHz, CDCl$_3$) δ 175.16, 167.16, 141.29, 137.80, 129.44, 129.31, 128.77, 128.64, 128.01, 127.88, 73.38, 72.12, 52.16, 32.99, 31.28, 16.86.
HRMS (ESI-TOF) m/z, Calcd for $C_{20}H_{21}O_4^+$ 341.1383, found 341.1383.
The absolute stereochemistry was assigned based on comparing the optical rotation of 3s with literature.

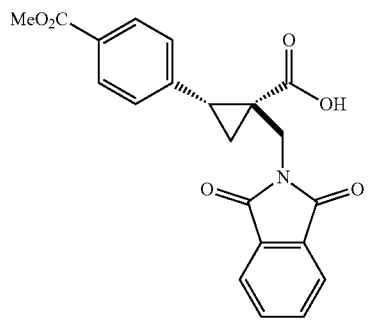 [SMILES: COC(=O)c1ccc([C@H]2C[C@@]2(CN2C(=O)c3ccccc3C2=O)C(=O)O)cc1]

(1R,2R)-1-((1,3-dioxoisoindolin-2-yl)methyl)-2-(4-(methoxycarbonyl)phenyl) cyclopropane-1-carboxylic acid (5l)
Substrate 4l was arylated following the general arylation (eluent: hexanes/ethyl acetate=1/1 with 1% v/v of acetic acid). The product was obtained as a white solid (71% yield).

The enantiomeric purity of the substrate was determined by SFC analysis (CHIRALPAK® IC column, 30% $^i$PrOH/CO$_2$, flow rate 2.0 mL/min, retention time 4.593 min (major) and 6.826 min (minor), 98:2 er);
$^1$H NMR (600 MHz, CDCl$_3$) δ 7.89 (d, J=8.4 Hz, 2H), 7.87-7.84 (m, 2H), 7.75-7.72 (m, 2H), 7.27 (d, J=8.4 Hz, 2H), 4.24 (d, J=14.6 Hz, 1 H), 4.50 (d, J al 14.6 Hz, 1H), 3.90 (s, 3H), 2.79.(t, J=8.3 Hz, 1H), 1.99 (dd, J=7.5, 5.5 Hz, 1H), 1.51 (dd, J=8.9, 5.6 Hz, 1H); $^{13}$C NMR (150 MHz, CDCl$_3$) δ 168.48, 167.15 140.94, 134.32, 132.01, 129.42, 129.28, 128.87, 123.67, 60.57, 52.18, 41.45, 32.88, 17.04;
HRMS (ESI-TOF) m/z Calced for $C_{21}H_{18}NO_8^+$ [M+H]$^+$ 380.1129, found 330.1136.
The absolute stereochemistry was assigned based on comparing the optical rotation of 3s with literature.

Enantioselective Arylation of 2-Aminoisobutyric Acid

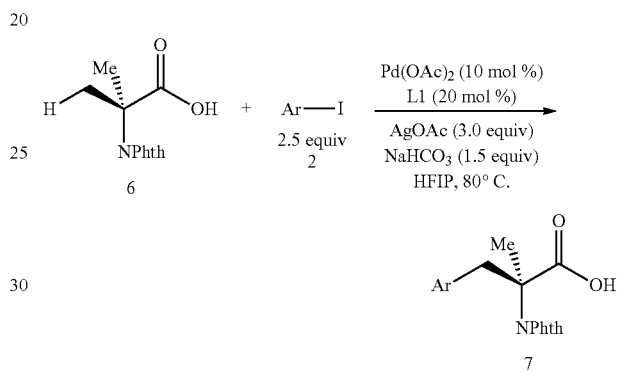

General procedure for enantioselective arylation of cyclopropanecarboxylic acid: A 2-dram vial equipped with a magnetic stir bar was charged with phthalyl-protect 2-aminoisobutyric acid (23.3 mg, 0.10 mmol), Pd(OAc)2 (2.2 mg, 10 mol %), L1 (4.4 mg, 20 mol %), AgOAc (50.0 mg, 0.30 mmol) and NaHCO$_3$ (12.6 mg, 0.15 mmol). Aryl iodide (0.25 mmol) was then added. Subsequently, HFIP (1.0 mL) was injected, and the vial was capped and closed tightly. The reaction mixture was then stirred at 80° C. for 24 h. The mixture was allowed to cool to room temperature and acetic acid (0.05 ml) was added. Then, the mixture was passed through a pad of Celite with ethyl acetate as the eluent to remove any insoluble precipitate. The resulting solution was concentrated.

For compound isolated as an acid: The residual mixture was dissolved with a minimal amount of acetone and loaded onto a preparative TLC plate. The pure acid product was then isolated using preparative TLC with ethyl acetatel-hexanes(1/1) with 1% w/w acetic acid as the eluent.

For compound isolated as an ester: The residual mixture was dissolved in 0.5 ml DMF. To the solution Cs$_2$CO$_3$ (99.7 mg, 0.3 mmol) and MeI (71.0 mg, 0.50 mmol, 31 µL) was added. The mixture was stirred at room temperature for 3 h and then was diluted with water followed by extraction with ethyl acetate. The organic layers were dried over Na$_2$SO$_4$, filtered and concentrated in vacuo. The residual mixture was dissolved with a minimal amount of acetone and loaded onto a preparative TLC plate. The pure ester product was then isolated using preparative TLC with ethyl acetate/toluene (1/20) as the eluent.

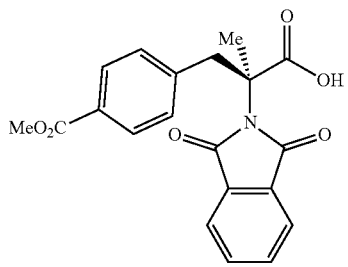 [SMILES: COC(=O)c1ccc(C[C@@](C)(C(=O)O)N2C(=O)c3ccccc3C2=O)cc1]

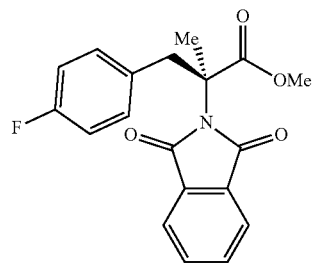 [SMILES: COC(=O)[C@](C)(Cc1ccc(F)cc1)N1C(=O)c2ccccc2C1=O]

(S)-2-(1,3-dioxolsoindolin-2-yl)-3-(4-(methoxycarbonyl)yphenyl)-2-methylpropanoic acid (7a)

Substrate 6 was arylated following the general acylation procedure. The product was isolated as acid and was obtained as a pale-yellow oil (65% yield).

The enantiomeric purity of the substrate was determined by SFC analysis (CHIRALPAK® IG-3 column, 25% (MeOH containing 0.5% HCO$_2$H)/CO$_2$, flow rate 4 mL/min, retention time 3.813 min (minor) and 4.373 min (major), 86:14 er);

$^1$H NMR (600 MHz, COCl$_3$) δ 7.85 (d, J=7.8 Hz, 2H), 7.78-7.76 (m, 2H), 7.72-7.70 (m, 2H), 7.13 (d, J=8.4 Hz, 2H), 3.86 (s, 3H), 3.83 (d, J=13.8 Hz, 1H), 3.27 (d, J=13.8, 1H), 1.95 (s, 3H); $^{13}$C NMR (150 MHz, CDCl$_3$) δ 168.45, 167.06, 141.11, 134.42, 131.45, 130.65, 129.69, 129.12, 123.52, 63.71, 52.19, 41.05, 21.97;

HRMS (ESI-TOF) m/z Calcd for C$_{20}$H$_{15}$NO$_6^+$ [m+H]$^+$0 368.1129, found 368.1131.

The absolute stereochemistry was assigned based on the X-ray crystallographic data of compounds 7f.

Methyl (S)-2-(1,3-dioxolsoindolin-2-yl)-3-(4-fluorophenyl)-2-methylpropanoate (7c)

Substrate 6 was arylated following the general arylation procedure. The product was isolated as ester and was obtained as a colorless oil (60% yield).

The enantiomeric purity of the substrate was determined by SFC analysis (CHIRALPAK® OJ-3 column, 5% PrOH/CO$_2$, flow rate 2.0 mL/min, retention time 2.868 min (minor) and 3.419 min (major), 89:11 er);

$^1$H NMR (600 MHz, CDCl$_3$) δ 7.79-7.76 (m, 2H), 7.73-7.70 (m, 2H), 7.04-7.00 (m, 2H), 6.7-6.84 (m, 2H), 3.75 (s, 3H), 3.75 (d, J=14.4 Hz, 1H), 3.23 (d, 14.4 Hz, 1H), 1.88 (s, 3H); $^{13}$C NMR (150 MHz, CDCl$_3$) δ 172.86, 168.47, 162,18 (d, J=244 Hz), 134.32, 132.04 (d, J=9 Hz), 131.59, 131.52 (d, J=4 Hz), 123.39, 115.26 (d, J=22 Hz), 64.05, 52.83, 20.65, 22.02; $^{19}$F NMR (376 MHz, CDCl$_3$) δ −115.88 (s, 1F);

HRMS (ESI-TOF) m/z Calcd for C$_{19}$H$_{17}$FNO$_4^+$ [M+H]$^+$ 342.1136, found 342.1148.

The absolute stereochemistry was assigned based on the X-ray crystallographic, data of compounds 7f.

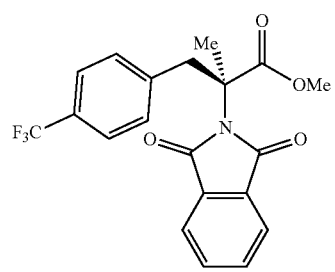

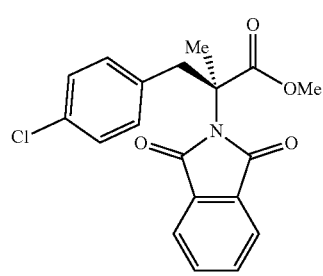

Methyl (S)-2-(1,3-dioxoisoindolin-2-yl)-2-methyl-3-(4-(trifluoromethyl)phenyl) proparloate (7b)

Substrate 6 was arylated following the general arylation procedure. The product was isolated as ester and was obtained as a colorless oil (67% yield).

The enantiomeric purity of the substrate was determined by SFC analysis (CHIRALPAK® AD-3 column, 3% PrOH/CO$_2$, flow rate 1.0 mL/min, retention time 14.292 min (major) and 15.855 min (minor), 87:13 er);

$^1$H NMR (600 MHz, CDCl$^3$) δ 7.90-7.77 (m, 2H), 7.75-7.71 (m, 2H), 7.43 (d, J=7.8 Hz, 2H), 7.19 (d, J=7.8 Hz, 2H), 3.84 (d, J=13.8 Hz, 1H), 3.75 (s, 3H), 3.34 (d, J=13.8 Hz, 1H), 1.90 (s, 3H); $^{13}$C NMR (150 MHz, CDCl$_3$) δ 172.62, 168.44, 140.01 (q, J=1.1 Hz), 134.43, 131.53, 130.96, 129.52 (q, J=32 Hz), 125.24 (q, J=3.5 Hz), 124.25 (q, J=270 Hz), 123.46, 63.86, 52.92, 41.32, 22.10; $^{19}$F NMR (376 MHz, CDCl3) δ −62.75 (s, 3F);

HRMS (ESI-TOF) m/z Calcd for C$_{21}$H$_{17}$F$_3$NO$_4^+$ [M+H]$^+$ 392.1104, found 392.1106.

The absolute stereochemistry was assigned based on the X-ray crystallographic data of compounds 7F.

Methyl (S)-3-(4-chlorophenyl)-2-(1,3-dioxolsoindolin-2-yl)-2-methylpropanoate (7d)

Substrate 6 was arylated following the general arylation procedure. The product was isolated as ester and was obtained as a pale-yellow solid (60% yield).

The enantiomeric purity of the substrate was determined by SFC analysis (CHIRALPAK® OJ-3 column. 5% $^i$PrOH/CO$_2$, flow rate 2.0 mL/min, retention time 3.660 min (minor) and 5.426 min (major), 91:9 er);

$^1$H NMR (600 MHz, CDCl$_3$) δ 7.80-7.76 (m, 2H), 7.74-7.71 (m, 2H), 7.14 (dt, J=8.4, 2.1 Hz, 2H), 6.99 (dt, J=8.4, 2:1 Hz, 2H), 3.75 (d, J=13.8 Hz; 1H), 3.75 (s, 3H), 3.24 (d, J=13.8 Hz, 1H), 1.88 (s, 3H); $^{12}$C NMR (150 MHz, CDCl$_3$) δ 172.78, 168.47,134,35, 134.31, 133.24, 131.89, 131.58, 128.54, 123.43, 63.96, 52.87, 40.84, 22.03;

HRMS (ESI-TOR) m/z Calcd for C$_{19}$H$_{17}$ClNO$_4^\delta$ [M+H]$^+$ 358.0841, found 358.0841.

The absolute stereochemistry was assigned based on the X-ray crystallographic data of compounds 7f.

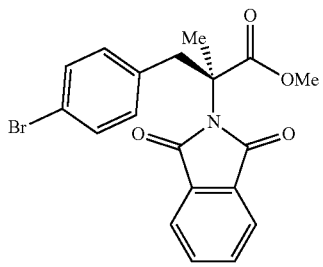 [SMILES: COC(=O)[C@](C)(Cc1ccc(Cl)cc1)N1C(=O)c2ccccc2C1=O]

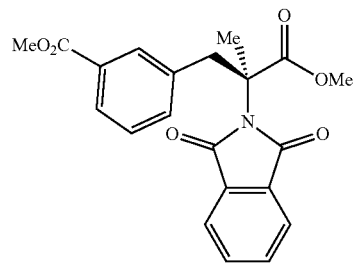

Methyl (S)-3-(4-bromophenyl)-2-(1,3-dioxolsoindolin-2-yl)-2-methylpropanoate (7e)

Substrate 6 was arylated following the general arylation procedure. The product was isolated as ester and was obtained as a white solid (65% yield).

The enantiomeric purity of the substrate was determined by SFC analysis (CHIRALPAK® OJ-3 column, 5% PrOH/ $CO_2$, flow rate 2.0 mL/min, retention time 4.313 min (minor) and 6.771 min (major), 92:8 er);

$^1$NMR (600 MHz, CDCl$_3$) δ 7.80-7.77 (m, 2H), 7.74-7.71 (m, 2H), 7.29 (d, J=7.8 Hz, 2H), 6.94 (d, J=8.4 Hz, 2H), 3.75-3.72 (m, 4H), 3.22 (d, J=13.8 Hz, 1H), 1.88 (s, 3H); $^{13}$C NMR (150 MHz, CDCl$_3$) δ 172.76, 168.46, 134.82, 134.36, 132.27, 131.57, 131.49, 123.44 121.39, 63.89, 52.88, 40.91, 22.02;

HRMS (ESI-TOF) m/z Calcd for $C_{19}H_{17}BrNO_4^+$ [M+H]$^+$ 402.0335, found 402.0341.

The absolute stereochemistry was assigned based on the X-ray crystallographic data of compounds 7f.

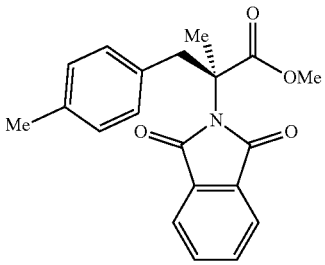 [SMILES: COC(=O)[C@](C)(Cc1ccc(C)cc1)N1C(=O)c2ccccc2C1=O]

Methyl (S)-2-(1,3-dioxolsoindolin-2-yl)-2-methyl-3-(p-tolyl)propanoate (7f)

Substrate 6 was arylated following the general arylation procedure. The product was isolated as ester and was obtained as a white solid (65% yield).

The enantiomeric purity of the substrate was determined by SFC analysis (CHIRALPAK® OJ-3 column, 5% $^i$PrOH/ $CO_2$, flow rate 2.0 mL/min, retention time 3.360 min (minor) and 5.523 min (major); 93:7 er);

$^1$H NMR (600 MHz, CDCl$_3$) δ 7.79-7.76 (m, 2H), 7.72-7.69 (m, 2H), 6.96 (d, J=7.8 Hz, 2H), 6.92 (d, J=8.4 Hz, 2H), 3.74 (d, J=13.8 Hz, 1H), 3.74 (s, 3H), 3.22 (d, J=13.8 Hz, 1H), 2.26 (s, 3H), 1.87 (s, 3H); $^{13}$C NMR (150 MHz, CDCl$_3$) δ 173.08, 168.55, 136.71, 134.19, 132.58, .131.73, 130.46, 129.06, 123.33, 64.28, 52.76, 40.96, 21.89, 21.20;

HRMS (ESI-TOF) Calcd for $C_{20}H_{20}NO_4^+$ [M+H]$^+$ 338.1387, found 338.1399.

The absolute stereochemistry was assigned based on the X-ray crystallographic data of compounds 7f.

(S)-2-(1,3-dioxolsoindolin-2-yl)-3-(3-(methoxycarbonyl) phenyl)-2-methylpropanoic acid (7g)

Substrate 6 was ariylated following the general arylation procedure. The product was isolated as acid and was obtained as a colorless oil (67% yield).

The enantiomeric purity of the substrate was determined by SFC analysis (CHIRALPAK® 3 column, 25% (MeOH containing 0.5% HCO$_2$H)/CO$_2$, flow rate 4 ML/min, retention time 3.052 min (minor) and 3.494 min (major), 86:14 er);

$^1$H NMR (600 MHz, CDCl$_3$) δ 7.86-7.84 (m, 1H), 7.75-7.72 (m, 2H), 7.70-7.68 (m, 3H), 7.24-7.23 (m, 2H), 3.77 (d, J=13.8 Hz, 1H), 3.72 (s, 3H), 3.22 (d, J=13.8 Hz, 1H), 1.90 (s, 3H);

$^{13}$C NMR (150 MHz, CDCl$_3$) δ 167.96, 166.31, 135.64, 134.49, 133.65, 129.58, 127.92; 127.88, 122.80, 63:34, 51.52, 40.20, 21.26; $^{13}$C NMR (150 MHz, CDCl$_3$) δ 176.90, 168.56, 166.91, 136.24, 135.09, 134,25, 131.63, 131.58, 130.18, 128.52, 128.49, 123.40, 63.94, 52.12, 40.80, 21.86;

HRMS (ESI-TOF) m/z Calcd for $C_{20}H_{18}NO_6^+$ [M+H]$^+$ 368.1129; found 368.1136.

The absolute stereochemistry was assigned based on the X-ray crystallographic data of compounds 7f.

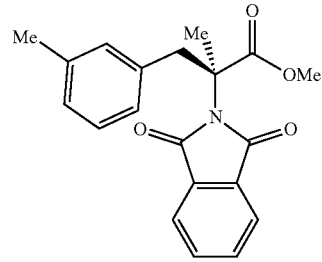 [SMILES: COC(=O)[C@](C)(Cc1cccc(C)c1)N1C(=O)c2ccccc2C1=O]

Methyl (S)-2-(1,3-dioxolsoindolin-2-yl)-2-methyl-3-(m-tolyl)propanoate (7h)

Substrate 6 was arylated following the general arylation procedure. The product was isolated as ester and was obtained as a colorless oil (65% yield).

The enantiomeric purity of the substrate was determined by SFC analysis (CHIRALPAK® OJ-3 column, 5% PrOH/ $CO_2$, flow rate 2.0 mL/min, retention time 3.367 min (minor) and 4.225 min (major), 92:8 er);

$^1$H NMR (600 MHz, CDCl$_3$) δ 7.79-7.75 (m, 2H), 7.72-7.69 (m, 2H), 7.05 (t, J=7.5 Hz, 1H), 6.98 (d, J=7.2 Hz, 1H), 6.84 (d, J=7.2 Hz, 1H), 6.81 (s, 1H), 3.75 (s, 3H), 3.73 (d, J=13.8 Hz, 1H), 3.20 (d, J=13.8 Hz, 1H), 2.12 (s, 3H), 1.88 (s, 3H); $^{13}$C NMR (150 MHz, CDCl$_3$) δ 173.11, 168.53, 137.80, 135.67, 134.19, 131.74, 131.49, 128.20, 127.90, 127.63, 123.29, 64.23, 52.77, 41.27, 21.95, 21.30.

HRMS (ESI-TOF) m/z Calcd for $C_{20}H_{20}NO_4^+$ [M+H]$^+$ 338.1387, found 338.1397.

The absolute stereochemistry was assigned based on the X-ray crystallographic data of compounds 7f.

Enantioselective Arylation of Drug Candidate

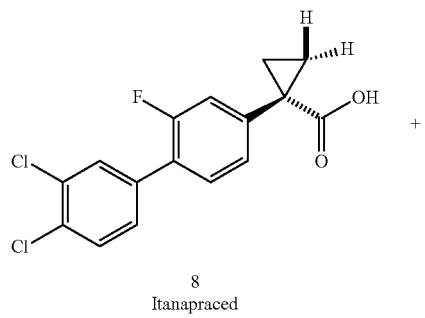

8
Itanapraced

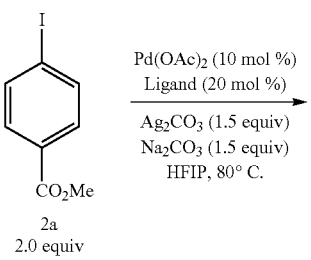

2a
2.0 equiv

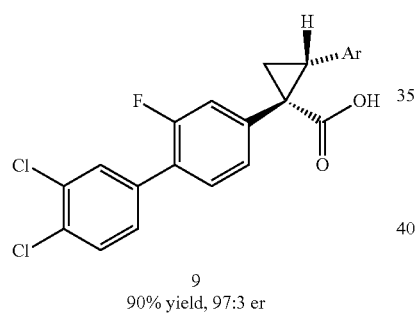

9
90% yield, 97:3 er

A 2-dram vial equipped with a magnetic stir bar was charged with Pd(OAc)2 (4.4 mg, 10 mol %) and L1 (8.8 mg, 20 mol %) in HFIP (0.25 ml). To the solution was added 8 (65.0 mg, 0.2 mmol). $Ag_2CO_3$ (82.7 mg, 0.30 mmol), $Na_2CO_3$ (31.8 mg, 0.30 mmol) and 2a (104.8 mg, 0.40 mmol) was then added. Subsequently, the vial was capped and closed tightly. The reaction mixture was then stirred at the rate of 200 rpm at 80° C. for 16 h. After being allowed to cool to room temperature, the mixture was diluted with ethyl acetate, and 0.1 ml of acetic acid was then added. The mixture was passed through a pad of Celit with ethyl acetate as the eluent to remove any insoluble precipitate. The resulting solution was concentrated, and the residual mixture was dissolved with a minimal amount of acetone and loaded onto a preparative TLC plate. The pure product was then isolated using preparative TLC with ethyl acetate and hexanes (1/1) as the eluent and 1% v/v of acetic acid as an additive. The product was obtained as a white solid (90% yield)

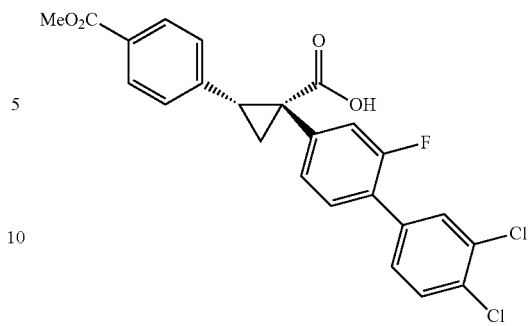

(1R,2R)-1-(3',4'-dichloro-2-fluoro-[1,1'-biphenyl]-4-(3-(methoxycarbonyl)phenyl) cyclopropane-1-carboxylic acid (9)

The enantiomeric purity of the substrate was determined by SFC analysis (CHIRALPAK® AD-3 column, 30% $^i$PrOH/$CO_2$, flow rate 2.0 mL/min, retention time 6.029 min (major) and 7.129 min (minor), 97:3 er);

$^1$H NMR (600 MHz, CDCl$_3$) δ 7.98 (d, J=8.4, 2H), 7.63 (s, 1H), 7.51 (d, J=8.4 Hz, 1), 7.38.-7.36 (m, 4H), 7.30 (d, J=7.8 Hz, 1H), 7.26 (d, J=10.8 Hz, 1H), 3.94 (s, 3H), 2.92 (t, J=8.4 Hz,1H), 2.32 (dd, J=6.9, 5.7 Hz, 1H), 1.75 (dd, J=8.7, 5.1 Hz, 1H); $^{13}$C NMR (150 MHz, CDCl$_3$) δ 175.21, 167.13, 159.28 (d, J=243 Hz), 141.66 (d, J=8 Hz), 140.79, 135.32, 132.80, 132.25, 130.88 (d, J=3 Hz), 130.61, 130.41 (d, J=3 Hz), 129.62, 129.36, 129.12, 128.38 (d, J3 Hz), 126.47 (d, J=3 Hz), 126.24 (d, J=12 Hz), 118.33 (d, J=22 Hz), 52.31, 37.29, 34.85, 19.59; $^{10}$F NMR (376 MHz. CDCl$_3$) δ −117.31 (s, 1F); HRMS (ESI-TOF) m/z Calcd for $C_{24}H_{18}Cl_2FO_4^+$ [M+H]$^+$ 459.0561, found 459.0584.

TABLE S1

| Crystal data and structure refinement for 7f. | |
|---|---|
| CDCC number | 1833926 |
| Empirical formula | $C_{20}H_{19}NO_4$ |
| Formula weight | 337.36 |
| Temperature | 100.0K |
| Wavelength | 1.54178 Å |
| Crystal system | Monoclinic |
| Space group | P 21 |
| Unit cell dimensions | a = 10.4618(5) Å  a = 90°. |
|  | b = 6.6429(3) Å  b = 112.484(2)°. |
|  | c = 12.8407(6) Å  g = 90°. |
| Volume | 824.55(7) Å$^3$ |
| Z | 2 |
| Density (calculated) | 1.359 Mg/m$^3$ |
| Absorption coefficient | 0.776 mm$^{-1}$ |
| F(000) | 356 |
| Crystal size | 0.28 × 0.2 × 0.18 mm$^3$ |
| Theta range for data collection | 3.725 to 69.101°. |
| Index ranges | −12 <= h <= 12, −8 <= k <= 8, −15 <= l <= 15 |
| Reflections collected | 11626 |
| Independent reflections | 3042 [R(int) = 0.0431] |
| Completeness to theta = 67.679° | 100.0% |
| Absorption correction | Semi-empirical from equivalents |
| Max. and min. transmission | 0.7531 and 0.6776 |
| Refinement method | Full-matrix least-squares on F$^2$ |
| Data/restraints/parameters | 3042/1/229 |
| Goodness-of-fit on F$^2$ | 1.076 |
| Final R indices [I > 2sigma(I)] | R1 = 0.0351, wR2 = 0.0893 |
| R indices (all data) | R1 = 0.0367, wR2 = 0.0909 |
| Absolute structure parameter | −0.05(12) |
| Extinction coefficient | n/a |
| Largest diff. peak and hole | 0.285 and −0.165 e.Å-3 |

1. K.-J.; Lin, D. W.; Miura, M.; Zhu, R.-Y.; Gong, w. Wasa, M.; Yu, J.-Q. *J. Am. Chem. Soc.* 2014, 136, 6138.

2. Li, J.; Luo, S.; Cheng. J. P. *J. Org. Chem.* 2009, 74, 1747.

3. Ishihara, K.; Nakano, K. *J. Am, Chem. Soc.* 2005, 127, 10504.

4. Nagamine, T.; Inomata, K; Endo, Y. *Heterocycles* 2008, 76, 1191.

5. Wasa, M.; Engle, K. M.; Lin, D. W.; Yoo, E. J.; Yu, J.-Q. *J. Am. Chem. Soc.* 2011, 133, 19598.

6. Santen Pharmaceutical Co., Ltd EP2119703 2009, A1.

7. Wyeth U.S patent No. 2008/255192 2008, A1

8. Giri, R.; Wasa, M.: Breazzano, S. P.; Yu, J.-Q. *Org. Lett*, 2006, 8, 5685.

9. Jahngen, E. G. E.; Phillips, D.; Kobelski, R. J.; Demko, D. M. *J. Org. Chem.* 1993, 48, 2472.

10. Chen, K.; Li, Z.-W.; Shen, P.-X,; Zhao, H.-W.; Shi, Z.-J. *Chem. Eur J.* 2018, 21, 7389.

11. Schiefer, I. T.; Abdul-Hay, S.; Wang, H; Vanni, M.; Qin, Z.; Thatcher, G. R. J. *J. Med. Chem.* 2011, 54, 2293.

12. Elling,G. R.; Hahn, R. C.; Schwab, G. *J. Am. Chem. Soc.* 1973, 17, 5669.

All patents and publications referred to herein are incorporated by reference herein to the same extent as if each individual publication was specifically and individually indicated to be incorporated by reference in its entirety.

What is claimed is:

1. A method of stereoselective arylation of a β-carbon atom of a cyclopropanecarboxylic acid having a β-hydrogen atom, the cyclopropanecarboxylic acid having either an α-substituent or having no α-substituent, comprising contacting the cyclopropanecarboxylic acid and an aryl iodide in the presence of a catalytic quantity of a Pd(II) salt, a molar equivalent or more on an Ag(I) basis of an Ag(I) salt, and a molar equivalent or more of a base, in 1,1,1,3,3,3-hexafluoroisopropanol solvent, in the presence of an single enantiomer, either (R) or (S), of an acetyl-protected aminoethyl amine (APAA) ligand of formula

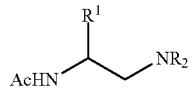

wherein Ac is acetyl, each R is independently selected methyl or ethyl, or the two R groups together with the nitrogen atom to which they are bonded form a 4- to 6-membered heterocyclyl ring; and wherein $R^1$ is an unsubstituted or substituted benzyl group, or wherein $R^1$ is a $(C_3-C_4)$-alkyl group;
  to stereoselectively provide a β-aryl-cyclopropanecarboxylic acid, wherein the arylated β-carbon atom of the β-aryl-cyclopropanecarboxylic acid product, when no α-substituent is present is of an (R) or (S) single enantiomeric configuration, respectively, and when an α-substituent is present is of an (S) or (R) single enantiomeric configuration, respectively; the aryl group introduced being disposed cis to the carboxylic acid group of the cyclopropanecarboxylic acid.

2. The method of claim 1 wherein the APAA ligand is of formula

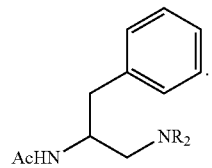

3. The method of claim 1 wherein the Pd(II) salt is Pd(OAc)$_2$.

4. The method of claim 1 wherein the carbonate base is Na$_2$CO$_3$, or wherein the Ag(I) salt is Ag$_2$CO$_3$, or both.

5. The method of claim 1 wherein the Pd(II) salt is present at about 10 mole %, the ligand is present at about 20 mole %, or both.

6. A method of stereoselective arylation of a β-carbon atom of 2-phthalimidoisobutryic acid, comprising contacting the 2-phthalimidoisobutryic acid and an aryl iodide in the presence of a catalytic quantity of a Pd(II) salt, a molar equivalent or more on an Ag(I) basis of an Ag(I) salt, and a molar equivalent or more of a base, in 1,1,1,3,3,3-hexafluoroisopropanol solvent, in the presence of an single enantiomer, either (R) or (S), of an acetyl-protected aminoethyl amine (APAA) ligand of formula

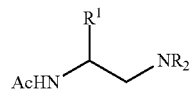

wherein Ac is acetyl, each R is independently selected methyl or ethyl, or the two R groups together with the nitrogen atom to which they are bonded form a 4- to 6-membered heterocyclyl ring; and wherein $R^1$ is an unsubstituted or substituted benzyl group, or wherein $R^1$ is a $(C_3-C_4)$-alkyl group;
  to stereoselectively provide a β-aryl-2-phthalimidoisobutryic acid, wherein the β-aryl-2-phthalimidoisobutryic acid product is of an (R) or (S) single enantiomeric configuration, respectively.

7. The method of claim 6 wherein the APAA ligand is of formula

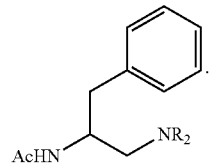

8. The method of claim 6 wherein the Pd(II) salt is Pd(OAc)$_2$.

9. The method of claim 6 wherein the carbonate base is Na$_2$CO$_3$, or wherein the Ag(I) salt is Ag$_2$CO$_3$, or both.

10. The method of claim 6 wherein the Pd(II) salt is present at about 10 mole %, the ligand is present at about 20 mole %, or both.

* * * * *